United States Patent [19]

Hamanaka et al.

[11] Patent Number: 5,389,666

[45] Date of Patent: Feb. 14, 1995

[54] FUSED BENZENEOXYACETIC ACID DERIVATIVES

[75] Inventors: Nobuyuki Hamanaka; Kanji Takahashi; Hidekado Tokumoto, all of Osaka, Japan

[73] Assignee: Ono Pharmaceutical Co., Ltd., Osaka, Japan

[21] Appl. No.: 997,492

[22] Filed: Dec. 28, 1992

[30] Foreign Application Priority Data

Dec. 27, 1991 [JP] Japan .................. 3-360502
Jul. 14, 1992 [JP] Japan .................. 4-209587

[51] Int. Cl.⁶ .................. A61K 31/415; C07D 233/70; C07D 261/00; C07D 263/00
[52] U.S. Cl. .................. 514/400; 514/398; 514/374; 514/378; 548/215; 548/240; 548/316.4
[58] Field of Search .................. 548/306.4, 316.4, 215, 548/240; 514/400

[56] References Cited

U.S. PATENT DOCUMENTS

| | | | |
|---|---|---|---|
| 4,349,684 | 9/1982 | Lautenschläger et al. | 548/320 |
| 4,367,235 | 1/1983 | Ross et al. | 548/302 |
| 4,492,708 | 1/1985 | Spitzer | 548/325 |
| 4,956,379 | 9/1990 | Meanwell | 548/378 |
| 5,011,851 | 4/1991 | Meanwell | 514/400 |

FOREIGN PATENT DOCUMENTS

| | | |
|---|---|---|
| 0013607 | 7/1980 | European Pat. Off. . |
| 0043292 | 1/1982 | European Pat. Off. . |
| 051829A1 | 5/1982 | European Pat. Off. . |
| 058580A1 | 9/1982 | European Pat. Off. . |
| 372445A1 | 6/1990 | European Pat. Off. . |
| 442448A3 | 8/1991 | European Pat. Off. . |
| 3504677 | 8/1986 | Germany . |

OTHER PUBLICATIONS

Br. J. Pharmac., 102, 1991, pp. 260-265.
Nature, vol. 263, Oct. 21, 1976, pp. 663-665.
Prostaglandins, vol. 12, No. 5, Nov. 1976, pp. 685-713.
Prostaglandins, vol. 12, No. 6, Dec. 1976, pp. 915-928.
Prostaglandins, vol. 13, No. 3, Mar. 1977, pp. 375-388.
Chemical & Engineering News, Dec. 20, 1976, pp. 17-19.
Br. J. Pharmac. 76, 1982, pp. 423-438.
Br. J. Pharmac. 84, 1985, pp. 595-607.
Br. J. Pharmac. 102, 1991, pp. 251-259.

*Primary Examiner*—Mukund J. Shah
*Assistant Examiner*—Pavanaram K. Sripada
*Attorney, Agent, or Firm*—Sughrue, Mion, Zinn, Macpeak & Seas

[57] ABSTRACT

A fused benzeneoxyacetic acid derivative of the formula (I):

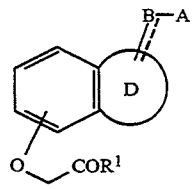

(I)

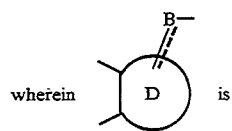

wherein D is

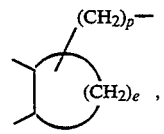
(i)

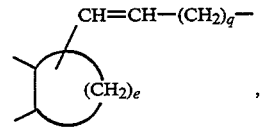

(ii)

(Abstract continued on next page.)

Abstract-continued

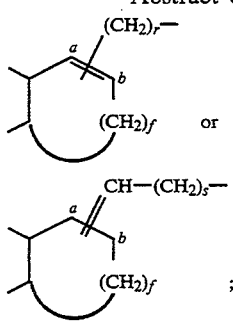

R[1] is OH, alkoxy, (alkyl)amino, residue of an amino acid;

A is phenyl, alkyl substituted by phenyl, residue of an imidazole, imidazole-2-yloxy(thio), 2-oxoimidazole, pyrazole, oxadiazole, oxazole, triazole, isoxazole or isothiazole, in the group of benzene may be substituted by one to three of alkyl, alkoxy, halogen, nitro or trihalomethyl;

e is 3–5;
f is 1–3;
p is 1–4;
q is 0–2;
r is 1–4;
s is 0–3)

and salts thereof possess an agonistic on $PGI_2$ receptor, so it is useful for prevention and/or treatment of thrombosis, arteriosclerosis, inchemic heart diseases, gastric alcer and hypertention.

12 Claims, No Drawings

FUSED BENZENEOXYACETIC ACID DERIVATIVES

SUMMARY

This invention is related to fused benzeneoxyacetic acid derivatives.

More particularly, this invention is related to:

1) fused benzeneoxyacetic acid derivatives of the formula (I):

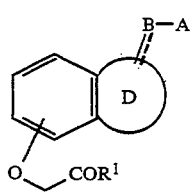

wherein all the symbols are the same meaning as hereafter defined, and non-toxic salts thereof and non-toxic acid addition salts thereof, 2) processes for the preparation thereof, and
3) pharmaceutical agents containing them as active ingredient.

BACKGROUND OF THE INVENTION

Prostaglandin $I_2$ ($PGI_2$) is a physiologically active natural substance having the following structural formula, which is biosynthesized from Prostaglandin $H_2$ ($PGH_2$) in the metabolic process in vivo called arachidonate cascade.

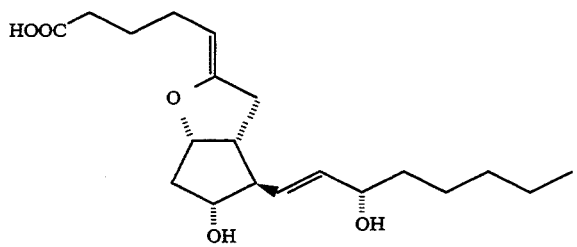

(see Nature, 263, 663(1976), Prostaglandins, 12, 685(1976), ibid, 12, 915(1976), ibid, 13, 375(1977) and Chemical and Engineering News, Dec. 20, 17(1976).

$PGI_2$ has been confirmed to possess not only a very strong inhibitory activity on blood platelet aggregation but a dissociative activity on blood platelet aggregation, an inhibitory activity on blood platelet adhesion, a vasodilating activity, an inhibitory activity on gastric acid secretion etc. Therefore, it has been considered that $PGI_2$ is useful for the prevention and/or the treatment for thrombosis, arteriosclerosis, ischemic heart diseases, gastric ulcer, hypertension etc. But its application for pharmaceuticals is limited because of its chemical instability and difficulty of separation of the actions according to purpose. Accordingly, various $PGI_2$ derivatives have been synthesized and many researches have been carried out for the maintenance and the separation of the actions. However, we have not necessarily satisfactory results yet.

Recently, in order to solve two problems above described, the research for $PGI_2$ receptor agonists which have a new-typed skeleton and may be useful for the treatment of or for the prevention of the above diseases, in view of $PGI_2$ receptor level, has been carried out.

RELATED ARTS

It has been reported in the literatures, that the following compounds not having the $PGI_2$ skeleton are $PGI_2$ receptor agonists which bind to a $PGI_2$ receptor and inhibit blood platelet aggregation:

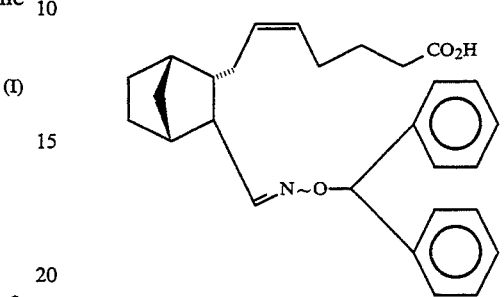

(see Brit. J. Pharmacol., 76, 423(1982), ibid, 84, 595(1985), and the Japanese Patent Kohyo No. 55-501098),

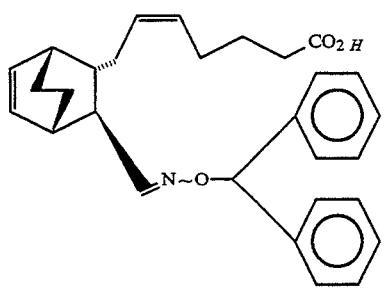

(see Brit. J. Pharmacol., 76, 423(1982), ibid, 84, 595(1985), and the Japanese Patent Kohyo No. 57-501127), and

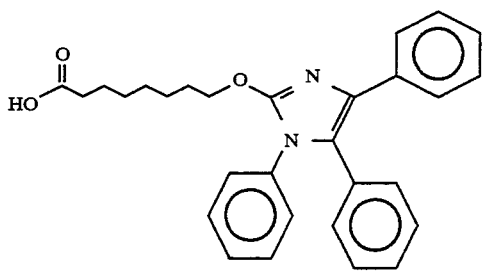

(see Brit. J. Pharmacol., 102, 251-266(1991) and the West German Patent Publication No. 3,504,677).

PURPOSE OF THE INVENTION

Energetic investigations have been carried out in order to discover new $PGI_2$ receptor agonists having a skeleton in chemical structure different from the compounds mentioned above, the present inventors have found that a kind of fused benzeneoxyacetic acid derivatives has an activity on binding to $PGI_2$ receptor and an inhibitory activity on blood platelet aggregation, and have accomplished the present invention.

The fused benzeneoxyacetic acid derivatives of the formula (I), of the present invention are quite novel, and it is not easy to predict from the above compounds already known as PGI2 receptor agonist, that the compounds of the present invention have an activity of PGI2 receptor agonist.

DETAILED DISCLOSURE OF THE INVENTION

The present invention is related to:

1) fused benzeneoxyacetic acid derivatives of the formula (I):

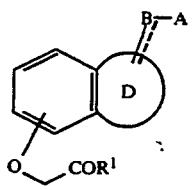
(I)

wherein 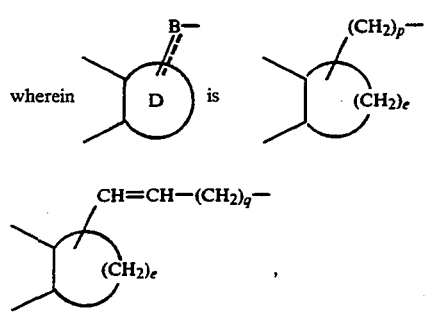 (i)

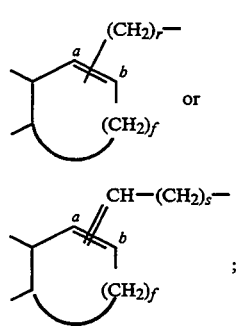 (ii)

(iii)

or (iv)

A is (i)

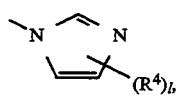

(ii)

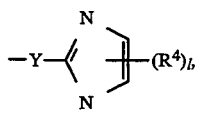

(iii)

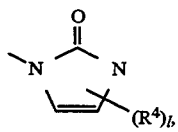

(iv)

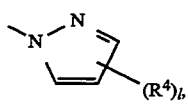

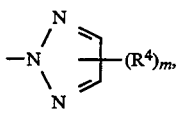 (vi)

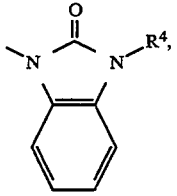 (vii)

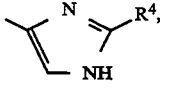 (viii)

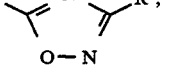 (ix)

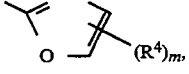 (x)

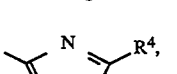 (xi)

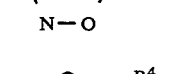 (xii)

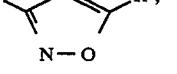 (xiii)

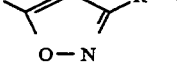 or (xiv)

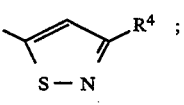 ; (xv)

$R^1$ is
(i) hydroxy,
(ii) $C_{1-12}$ alkoxy or
(iii) $NR^2R^3$;

$R^2$ and $R^3$ each, independently, is
(i) hydrogen atom or
(ii) $C_{1-4}$ alkyl; or $R^2$ and $R^3$, taken together with nitrogen atom bond to $R^2$ and $R^3$ are the residue of an amino acid;

$R^4$ each, independently, is
(i) hydrogen atom,
(ii) $C_{1-4}$ alkyl,
(iii) phenyl or
(iv) $C_{1-4}$ alkyl substituted by one or two ring optionally selected from 4–7 membered monocyclic hetero ring containing one or two nitrogen atom, and phenyl;

the said phenyl and hetero rings may also be substituted by one to three of $C_{1-4}$ alkyl, $C_{1-4}$ alkoxy, halogen atom, nitro or trihalomethyl, when R⁴ is phenyl or the group containing phenyl or 4-7 membered monocyclic hetero ring containing one or two nitrogen atom, Y is oxygen atom or sulfur atom;
e is 3-5;
f is 1-3;
l is 1-3;
m is 1 or 2;
p is 1-4;
q is 0-2;
r is 1-4;
s is 0-3;
with the proviso that,
(1) when A is

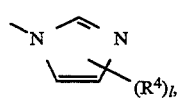 (i)

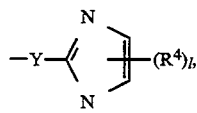 (ii)

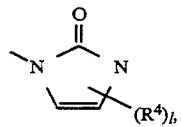 (iii)

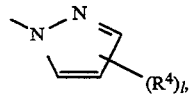 (iv)

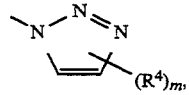 (v)

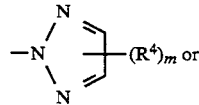 (vi)

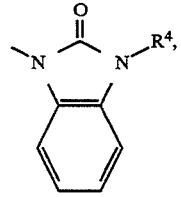 (vii)

wherein all the symbols are the same meaning hereinbefore defined, or

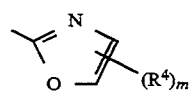 (x)

wherein R⁴ is hydrogen atom,
q or s is not zero;
(2) when A is

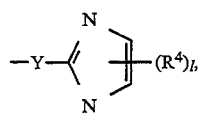 (ii)

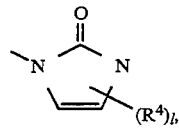 (iii)

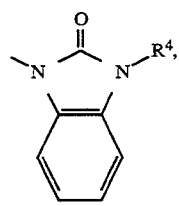 (vii)

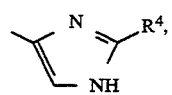 (viii)

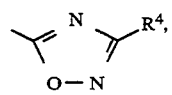 (ix)

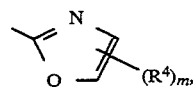 (x)

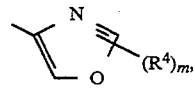 (xi)

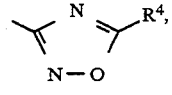 (xii)

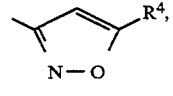 (xiii)

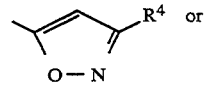 (xiv)

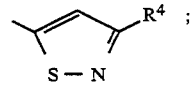 (xv)

wherein Y, l and m are the same meaning as hereinbefore defined, and R⁴ is $C_{1-4}$ alkyl substituted by hetero ring, a hetero ring in R⁴ should be bonded to the alkyl via a carbon atom in the hetero ring;
(3) —(CH₂)ᵣ- or =CH—(CH₂)ₛ— should be bonded to the carbon atom at the position a or b in the ring;
(4) when A is

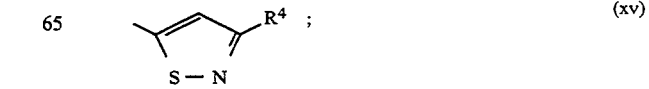 (xv)

wherein R⁴ is the same meaning as hereinbefore defined,

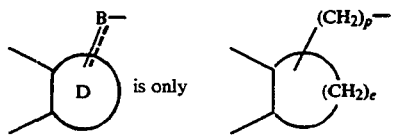

in which p and e are the same meaning as hereinbefore defined; and non-toxic salts thereof and non-toxic acid addition salts thereof;
2) processes for the preparation thereof and
3) pharmaceutical agents containing them as active ingredient.

Unless otherwise specified, all isomers are included in the present invention. For example, alkyl, alkoxy, alkylene and alkenylene include straight and branched ones. Double bond in alkenylene includes E, Z and EZ mixture. Isomers generated by asymmetric carbon atoms, e.g., branched alkyl are included in the present invention.

The compounds of the formula (I) of the present invention, wherein R¹ is hydroxy may be converted into the corresponding salts by methods known per se. Non-toxic and water-soluble salts are preferable. Suitable salts, for example, are salts of alkaline metal (potassium, sodium etc.), salts of alkaline earth metal (calcium, magnesium etc.), ammonium salts, salts of pharmaceutically-acceptable organic amine (tetramethylammonium, triethylamine, methylamine, dimethylamine, cyclopentylamine, benzylamine, phenethylamine, piperidine, monoethanolamine, diethanolamine, tris (hydroxymethyl)amine, lysine, arginine, N-methyl-D-glucamine etc.).

The compounds of the formula (I) may be converted into the corresponding acid additional salts by methods known per se. Non-toxic and water-soluble salts are preferable. Suitable acid addition salts, for example, are salts of inorganic acids, e.g., hydrochloride, hydrobromide, sulphate, phosphate, nitrate etc., or salts of organic acids, e.g., acetate, lactate, tartarate, oxalate, fumarate, maleate, citrate, benzoate, methanesulphonate, ethanesulphonate, benzenesulphonate, toluenesulphonate, isethioate, glucuronate, gluconate etc.

The compounds of the formula (I), salts thereof or acid additional salts thereof may be converted into hydrate thereof by methods known per se.

In the formula (I), $C_{1-12}$ alkoxy represented by $R^1$ means methoxy, ethoxy, propoxy, butoxy, pentyloxy, hexyloxy, heptyloxy, octyloxy, nonyloxy, decyloxy, undecyloxy, dodecyloxy and isomers thereof. $C_{1-4}$ alkyl represented by $R^2$, $R^3$ and $R^4$, means methyl, ethyl, propyl, butyl and isomers thereof.

In the formula (i), 4-7 membered monocyclic hetero ring containing one or two nitrogen atom, represented by $R^4$ means pyrrole, pyridine, azepine, imidazole, pyrazole, pyrazine, pyrimidine, pyradazine, diazepine and partially or fully saturated ring thereof.

$C_{1-4}$ alkyl as substituents of a phenyl or hetero ring in the group represented by $R^4$ mean methyl, ethyl, propryl, butyl and isomers thereof. $C_{1-4}$ alkoxy mean methoxy, ethoxy, propoxy, butoxy and isomers thereof.

Halogen atom and halogen atom in trihalomethyl mean fluorine, chlorine, bromine and iodine atoms.

Example of representative compounds of the formula (I), of the present invention are listed as follows:

[2-(Imidazol-1-yl)methyl-2,3-dihydroinden-4-yloxy]acetic acid,
[1-[2-(4-Phenylmethylimidazol-1-yl)ethyl]-1,2,3,4-tetrahydronaphthalen-5-yloxy]acetic acid,
[1-[3-(4-Phenylmethylimidazol-1-yl)-1-propenyl]-1,2,3,4-tetrahydronaphthalen-5-yloxy]acetic acid,
[1-[2-(4-Phenylmethylimidazol-1-yl)ethyl]-3,4-dihydronaphthalen-5-yloxy]acetic acid,
[1-[2-(4-Phenylmethylimidazol-1-yl)ethylidene]-1,2,3,4-tetrahydronaphthalen-5-yloxy]acetic acid,
[2-(1-Diphenylmethylimidazol-2-yloxy)methyl-1,2,3,4-tetrahydronaphthalen-6-yloxy]acetic acid,
[2-[3-(1-Diphenylmethylimidazol-2-yloxy)-1-propenyl]-1,2,3,4-tetrahydronaphthalen-5-yloxy]acetic acid,
[2-(1-Diphenylmethylimidazol-2-yloxy)methyl-3,4-dihydronaphthalen-5-yloxy]acetic acid,
[1-[2-(1-Diphenylmethylimidazol-2-yloxy)ethylidene]-1,2,3,4-tetrahydronaphthalen-5-yloxy]acetic acid,
[2-(4-Diphenylmethylimidazol-2-ylthio)methyl-1,2,3,4-tetrahydronaphthalen-5-yloxy]acetic acid,
[2-[3-(4-Diphenylmethylimidazol-2-ylthio)-1-propenyl]-1,2,3,4-tetrahydronaphthalen-5-yloxy]acetic acid,
[2-(4-Diphenylmethylimidazol-2-ylthio)methyl-3,4-dihydronaphthalen-5-yloxy]acetic acid,
[1-[2-(4-Diphenylmethylimidazol-2-ylthio)ethylidene]-1,2,3,4-tetrahydronaphthalen-5-yloxy]acetic acid,
[2-[2-(2-Oxo-4-diphenylmethylimidazol-1-yl)ethyl]-1,2,3,4-tetrahydronaphthalen-5-yloxy]acetic acid,
[2-[3-(2-Oxo-4-diphenylmethylimidazol-1-yl)-1-propenyl]-1,2,3,4-tetrahydronaphthalen-5-yloxy]acetic acid,
[2-[2-(2-Oxo-4-diphenylmethylimidazol-1-yl)ethyl]-3,4-dihydronaphthalen-5-yloxy]acetic acid,
[1-[2-(2-Oxo-4-diphenylmethylimidazol-1-yl)ethylidene]-1,2,3,4-tetrahydronaphthalen-5-yloxy]acetic acid,
[2-(3,4,5-Triphenylpyrazol-1-yl)methylbenzocycloheptan-6-yloxy]acetic acid,
[2-[4-((3-Chlorophenyl)phenylmethyl)pyrazol-2-yl]methyl-1,2,3,4-tetrahydronaphthalen-5-yloxy]acetic acid,
[2-[3-[4-((3-Chlorophenyl)phenylmethyl)pyrazol-2-yl]-1-propeny]-1,2,3,4-tetrahydronaphthalen-5-yloxy]acetic acid,
[2-[4-((3-Chlorophenyl)phenylmethyl)pyrazol-2-yl]methyl-3,4-dihydronaphthalen-5-yloxy]acetic acid,
[1-[2-[4-((3-Chlorophenyl)phenylmethyl)pyrazol-2-yl]ethylidene]-1,2,3,4-tetrahydronaphthalen-5-yloxy]acetic acid,
[2-[3-((4-Diphenylmethyl)-1,2,3-triazol-2-yl)-1-propenyl]-1,2,3,4-tetrahydronaphthalen-5-yloxy]acetic acid,
[2-((4-Diphenylmethyl)-1,2,3-triazol-1-yl)methyl-3,4-dihydronaphthalen-5-yloxy]acetic acid,
[1-[2-((4-Diphenylmethyl)-1,2,3-triazol-3-yl)ethylidene]-1,2,3,4-tetrahydronaphthalen-5-yloxy]acetic acid,
[2-(1,2,4-Oxadiazin-5-yl)methyl-1,2,3,4-tetrahydronaphthalen-5-yloxy]acetic acid,
[2-[2-(1,2,4-Oxadiazin-5-yl)ethenyl]-1,2,3,4-tetrahydronaphthalen-5-yloxy]acetic acid,
[2-(1,2,4-Oxadiazin-5-yl)methyl-3,4-dihydronaphthalen-5-yloxy]acetic acid,
[1-[2-(1,2,4-Oxadiazin-5-yl)ethylidene]-1,2,3,4-tetrahydronaphthalen-5-yloxy]acetic acid,
[2-[3-(3-Phenyl-1,2,4-oxadiazol-5-yl)propyl]-2,3-dihydroinden-4-yloxy]acetic acid,

[2-[2-(Oxazol-2-yl)ethyl]-1,2,3,4-tetrahydronaphthalen-5-yloxy]acetic acid,
[2-[2-(Oxazol-2-yl)ethenyl]-1,2,3,4-tetrahydronaphthalen-5-yloxy]acetic acid,
[2-[2-(Oxazol-2-yl)ethyl]-3,4-dihydronaphthalen-5-yloxy]acetic acid,
[1-[2-(Oxazol-2-yl)ethylidene]-1,2,3,4-tetrahydronaphthalen-5-yloxy]acetic acid,
[2-[2-[4-(3-Trifluoromethylphenyl)oxazol-2-yl]ethyl]-1,2,3,4-tetrahydronaphthalen-5-yloxy]acetic acid,
[2-[2-[4-(3-Trifluoromethylphenyl)oxazol-2-yl]ethenyl]-1,2,3,4-tetrahydronaphthalen-5-yloxy]acetic acid,
[2-[2-[4-(3-Trifluoromethylphenyl)oxazol-2-yl]ethyl]-3,4-dihydronaphthalen-5-yloxy]acetic acid,
[1-[2-[4-(3-Trifluoromethylphenyl)oxazol-2-yl]ethylidene]-1,2,3,4-tetrahydronaphthalen-5-yloxy]acetic acid,
[1-[2-(Oxazol-4-yl)ethyl]-1,2,3,4-tetrahydronaphthalen-5-yloxy]acetic acid,
[1-[2-(2-((3-Pyridyl)phenylmethyl)oxazol-4-yl)ethenyl]-1,2,3,4-tetrahydronaphthalen-5-yloxy]acetic acid,
[1-[2-(2-((3-Pyridyl)phenylmethyl)oxazol-4-yl)ethyl]-3,4-dihydronaphthalen-5-yloxy]acetic acid,
[1-[2-(2-((3-Pyridyl)phenylmethyl)oxazol-4-yl)ethylidene]-1,2,3,4-tetrahydronaphthalen-5-yloxy]acetic acid,
[1-[2-(3-Nitrophenyl)oxazol-4-yl)methyl-1,2,3,4-tetrahydronaphthalen-5-yloxy]acetic acid,
[1-[2-(2-(3-Nitrophenyl)oxazol-4-yl)ethenyl]-1,2,3,4-tetrahydronaphthalen-5-yloxy]acetic acid,
[1-[2-(3-Nitrophenyl)oxazol-4-yl)methyl-3,4-dihydronaphthalen-5-yloxy]acetic acid,
[1-[2-(2-(3-Nitrophenyl)oxazol-4-yl)ethylidene]-1,2,3,4-tetrahydronaphthalen-5-yloxy]acetic acid,
[2-(Imidazol-4-yl)methyl-1,2,3,4-tetrahydronaphthalen-5-yloxy]acetic acid,
[2-(2-(Imidazol-4-yl)ethenyl)-1,2,3,4-tetrahydronaphthalen-5-yloxy]acetic acid,
[2-(Imidazol-4-yl)methyl-3,4-dihydronaphthalen-5-yloxy]acetic acid,
[1-(2-(Imidazol-4-yl)ethylidene)-1,2,3,4-tetrahydronaphthalen-5-yloxy]acetic acid,
[2-[3-[4-((1-Imidazolyl)phenylmethyl)pyrazol-2-yl]-1-propenyl]-1,2,3,4-tetrahydronaphthalen-5-yloxy]acetic acid,
[2-[4-((1-Imidazolyl)phenylmethyl)pyrazol-2-yl]methyl-3,4-dihydronaphthalen-5-yloxy]acetic acid,
[1-[2-[4-((1-Imidazolyl)phenylmethyl)pyrazol-2-yl]ethylidene]-1,2,3,4-tetrahydronaphthalen-5-yloxy]acetic acid,
[1-[3-(5-Diphenylmethyl-1,2,4-oxadiazol-3-yl)-1-propenyl]-1,2,3,4-tetrahydronaphthalen-5yloxy]acetic acid,
[1-[2-(5-Diphenylmethyl-1,2,4-oxadiazol-3-yl)ethyl]-3,4-dihydronaphthalen-5-yloxy]acetic acid,
[1-[2-(5-Diphenylmethyl-1,2,4-oxadiazol-3-yl)ethylidene]-1,2,3,4-tetrahydronaphthalen-5-yloxy]acetic acid,
[2-[2-(5-Diphenylmethylisoxazol-3-yl)ethenyl]-1,2,3,4-tetrahydronaphthalen-5-yloxy]acetic acid,
[2-(5-Diphenylmethylisoxazol-3-yl)methyl-3,4-dihydronaphthalen-5-yloxy]acetic acid,
[1-[2-(5-Diphenylmethylisoxazol-3-yl)ethylidene]-1,2,3,4-tetrahydronaphthalen-5-yloxy]acetic acid,
[2-[2-(3-Diphenylmethylisoxazol-5-yl)ethenyl]-1,2,3,4-tetrahydronaphthalen-5-yloxy]acetic acid,
[2-(3-Diphenylmethylisoxazol-5-yl)methyl-3,4-dihydronaphthalen-5-yloxy]acetic acid,
[1-[2-(3-Diphenylmethylisoxazol-5-yl)ethylidene]-1,2,3,4-tetrahydronaphthalen-5-yloxy]acetic acid,
[2-[(4-((3-Pyrrolyl)phenylmethyl)pyrazol-1-yl)methyl]-1,2,3,4-tetrahydronaphthalen-5-yloxy]acetic acid,
[2-[(4-((2-Imidazolyl)phenylmethyl)pyrazol-1-yl)methyl]-1,2,3,4-tetrahydronaphthalen-5-yloxy]acetic acid,
[2-[(4-((4-Pyrazolyl)phenylmethyl)pyrazol-1-yl)methyl]-1,2,3.4-tetrahydronaphthalen-5-yloxy] acetic acid,
[2-[(4-(Di(3-pyridyl)methyl)pyrazol-1-yl)methyl]-1,2,3,4-tetrahydronaphthalen-5-yloxy]acetic acid,
[2-[(4-((3-Pyrimidinyl)phenylmethyl)pyrazol-1-yl)methyl]-1,2,3,4-tetrahydronaphthalen-5-yloxy]acetic acid,
[2-[(4-((2-Pyrazinyl)phenylmethyl)pyrazol-1-yl)methyl]-1,2,3,4-tetrahydronaphthalen-5-yloxy]acetic acid,
[2-[(4-((4-Pyridazinyl)phenylmethyl)pyrazol-1-yl)methyl]-1,2,3,4-tetrahydronaphthalen-5-yloxy]acetic acid,
[2-[(4-((3-Azepinyl)phenylmethyl)pyrazol-1-yl)methyl]-1,2,3,4-tetrahydronaphthalen-5-yloxy]acetic acid,
[2-[(4-((1,3-Diazepin-5-yl)phenylmethyl)pyrazol-1-yl)methyl]-1,2,3,4-tetrahydronaphthalen-5-yloxy]acetic acid, and those described in examples below, and further, non-toxic salts thereof and non-toxic acid addition salts thereof.

Processes for the Preparation of the Compounds of the Present Invention in the compounds of the present invention, of the formula (I), (1) compounds of the formula (I-1):

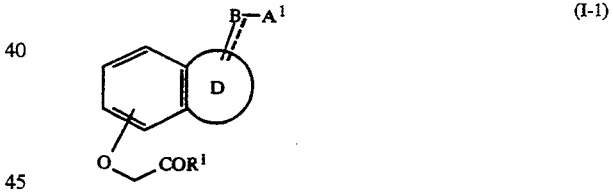

wherein $A^1$ is the same meaning as A, with the proviso that, in the group represented by $R^4$ in A, a hetero ring as a substituent of $C_{1-4}$ alkyl should be bonded to the alkyl via a carbon atom in the hetero ring, and the other symbols are the same meaning as hereinbefore defined, may be prepared:

(A) by reacting a compound of the formula (III):

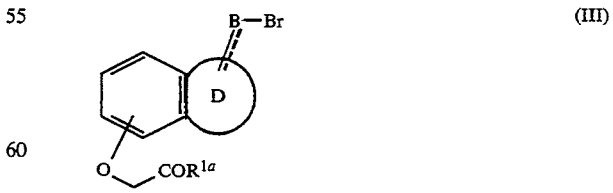

wherein $R^{1a}$ is methoxy or ethoxy and the other symbols are the same meaning as hereinbefore defined, with the compound of the formula (a)

$$HA^a \qquad (a)$$

wherein $A^a$ is

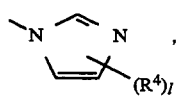

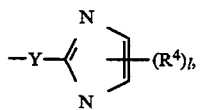

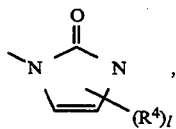

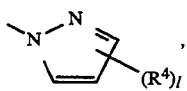

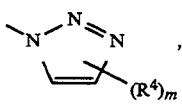

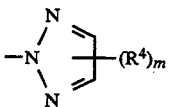

or

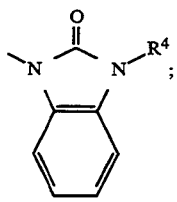

wherein all the symbols are the same meaning as hereinbefore defined, (B) by reacting a compound formula (III):

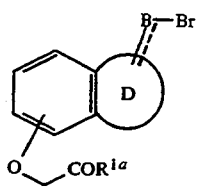

wherein all the symbols are the same meaning as hereinbefore defined, with an oxazole, (C) by the cyclization of a compound of the formula (V):

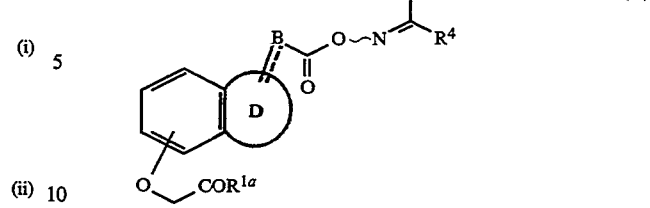

wherein all the symbols are the same meaning as hereinbefore defined, (D) by reacting a compound of the formula (VIII):

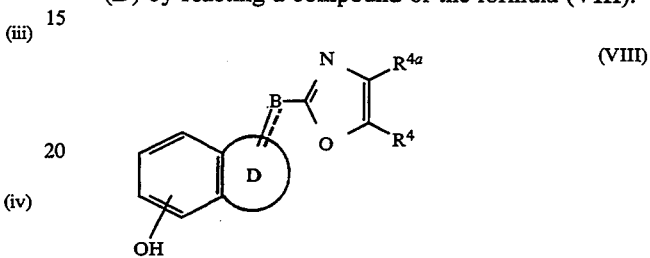

wherein $R^{4a}$ is (i) $C_{1-4}$ alkyl, (ii) phenyl or (iii) $C_{1-4}$ alkyl substituted by one or two ring optionally selected from 4–7 membered monocyclic hetero ring containing one or two nitrogen atom, and phenyl, and the other symbols are the same meaning as hereinbefore defined, with the compound of the formula (b):

$$BrCH_2COR^{1a} \quad (b)$$

wherein $R^{1a}$ is the same meaning as hereinbefore defined, (E) by reacting a compound of the formula (IX):

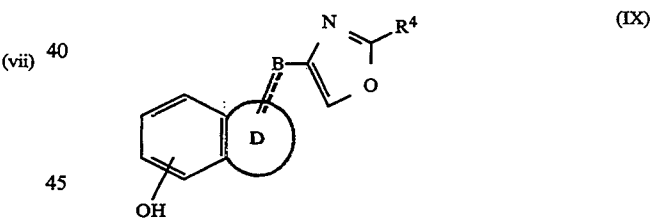

wherein all the symbols are the same meaning as hereinbefore defined, with the compound of the formula (b):

$$BrCH_2COR^{1a} \quad (b)$$

wherein $R^{1a}$ is the same meaning as hereinbefore defined, (F) by reacting a compound of the formula (XI):

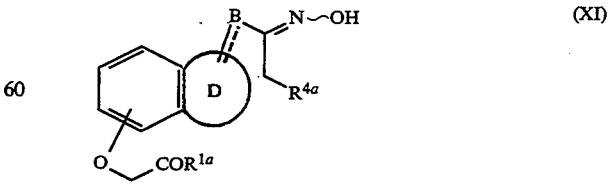

wherein all the symbols are the same meaning as hereinbefore defined, with the compound of the formula (c):

$$R^4COCl \quad (c)$$

wherein $R^4$ is the same meaning as hereinbefore defined, (G) by reacting a compound of the formula (XII):

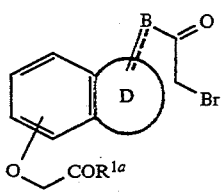

(XII)

wherein all the symbols are the same meaning as hereinbefore defined, with the compound of the formula (d):

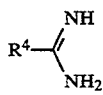

(d)

wherein $R^4$ is the same meaning as hereinbefore defined, (H) by the cyclization of a compound of the formula (XIV):

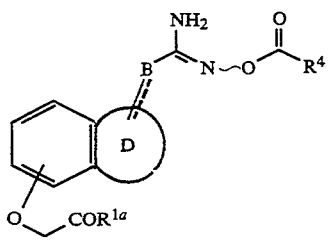

(XIV)

wherein all the symbols are the same meaning as hereinbefore defined, (I) by reacting a compound of the formula (XVI):

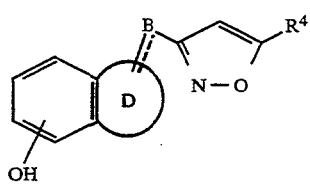

(XVI)

wherein all the symbols are the same meaning as hereinbefore defined, with the compound of the formula (b):

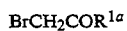

(b)

wherein $R^{1a}$ is the same meaning as hereinbefore defined, (J) by reacting a compound of the formula (XIX):

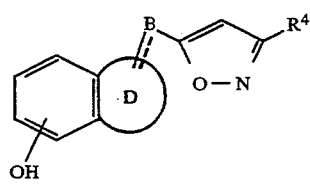

(XIX)

wherein all the symbols are the same meaning as hereinbefore defined, with the compound of the formula (b):

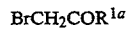

(b)

wherein $R^{1a}$ is the same meaning as hereinbefore defined, (K) by reacting a compound of the formula (XX):

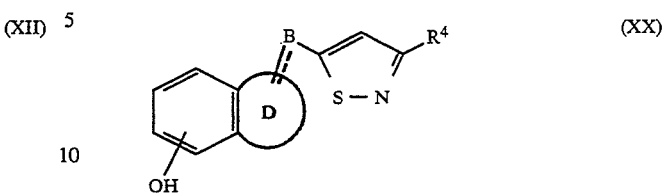

(XX)

wherein all the symbols are the same meaning as hereinbefore defined, with the compound of the formula (b):

(b)

wherein $R^{1a}$ is the same meaning as hereinbefore defined, (L) by the hydrolysis of an ester bond in a compound of the formula (Ia):

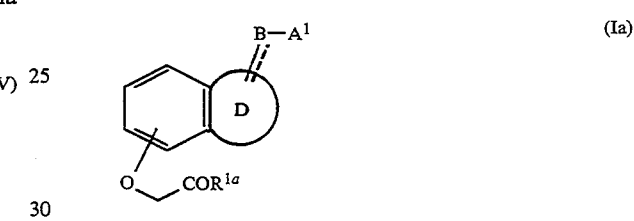

(Ia)

wherein all the symbols are the same meaning as hereinbefore defined, (M) by subjecting a compound of the formula (Ib):

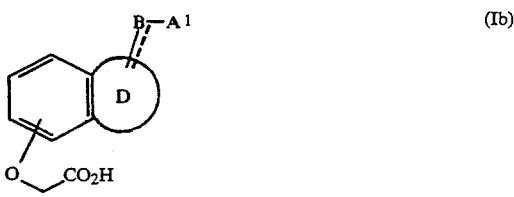

(Ib)

wherein all the symbols are the same meaning as hereinbefore defined, to form an acyl chloride, and then by the reaction of the compound thus obtained with the compound of the formula (f):

(f)

wherein $R^{1b}$ is $C_{3-12}$ alkyl, or (N) by subjecting a compound of the formula (Ib):

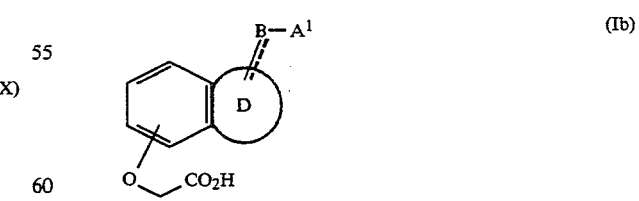

(Ib)

wherein all the symbols are the same meaning as hereinbefore defined, to form an acyl chloride, and then by the reaction of the compound thus obtained with the compound of the formula (g):

(g)

wherein $R^2$ and $R^3$ are the same meaning as hereinbefore defined.

The reaction (A) may be carried out in an appropriate organic solvent (e.g., dimethylformamide) in the presence of an appropriate base (e.q., sodium hydride).

The reaction (B) may be carried out in an appropriate organic solvent (e.g., tetrahydrofuran)in the presence of an appropriate base (e.q., n-butyllithium).

The reaction (C) and (H) may be carried out in an appropriate organic solvent (e.g., toluene) at 20° C.

The reaction (D), (E), (I), (J) and (K) may be carried out in an appropriate organic solvent (e.g., acetone) in the presence of an appropriate base (e.q., potassium carbonate).

The reaction (F) may be carried out at 100° C.

The reaction (G) may be carried out in an appropriate organic solvent (e.g., chloroform) at 70° C.

The reaction (L) may be carried out in an appropriate solvent (e.g., methanol, tetrahydrofuran), using a hydroxide or a carbonate of an alkaline metal.

The reaction (M) and (N) may be carried out by reacting a compound of the formula (Ib) with an acyl halide such as oxalyl chloride, thionyl chloride in an appropriate solvent (e.g., methylene chloride), and then by reacting a compound thus obtained with an alcohol of the formula (f) and an amine of the formula (g), respectively, in an appropriate solvent (e.g., methylene chloride), in the presence of an appropriate base (e.q., triethylamine) at 0° to 40° C.

The compounds of formulae (III), (V), (VIII), (IX), (XI), (XII), (XIV), (XVI), (XIX), (XX), (Ia) and (Ib) may be prepared by using a series of reactions depicted in the following scheme.

The compounds of the formulae (a), (b), (c), (d), (f) and (g) are well known per se, and may be obtained commercially as reagents or may be easily prepared by methods known per se.

Scheme [A]

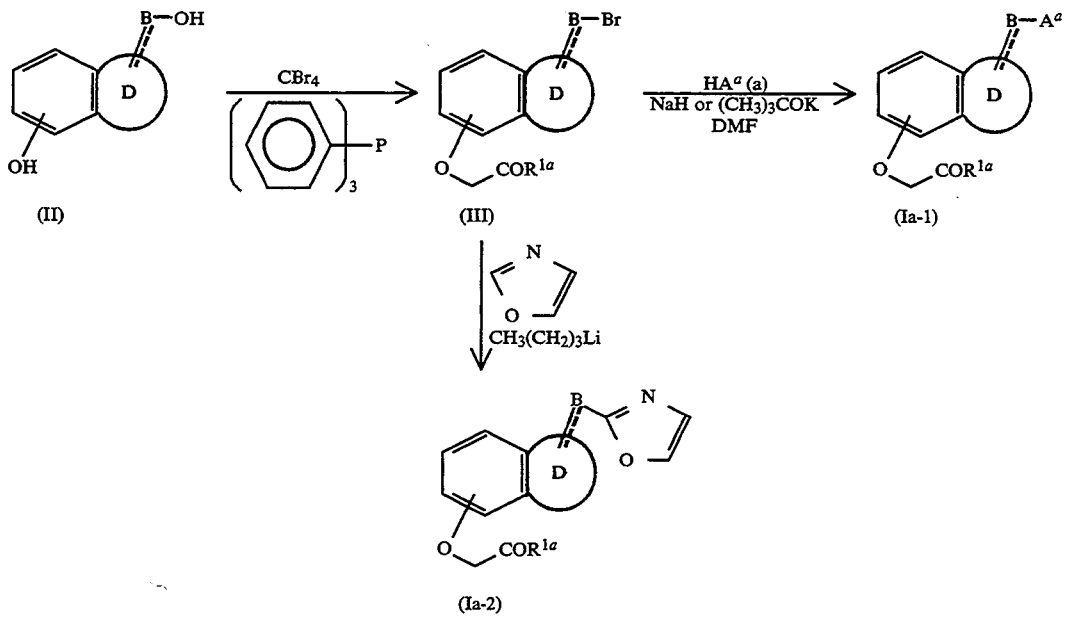

Scheme [B]

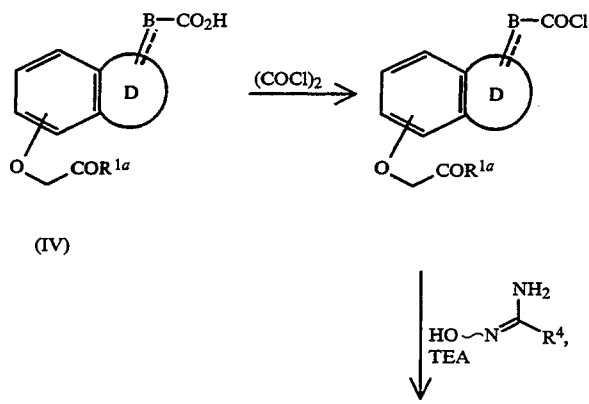

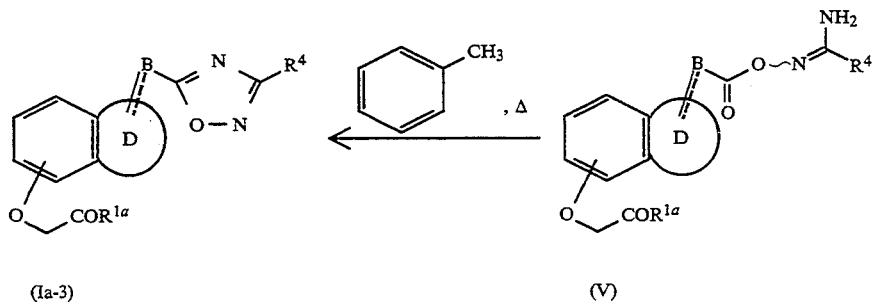
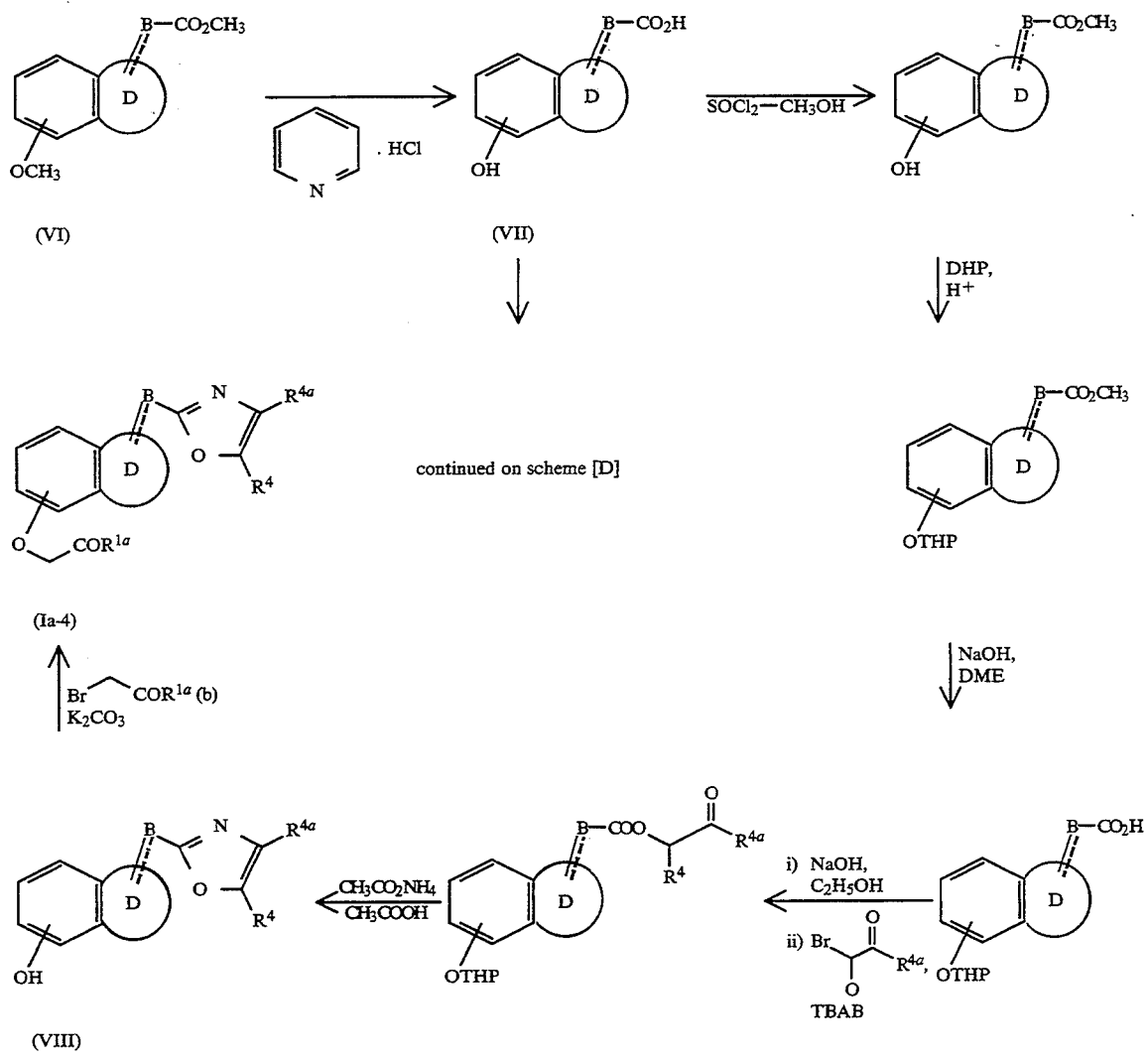

Scheme [D]
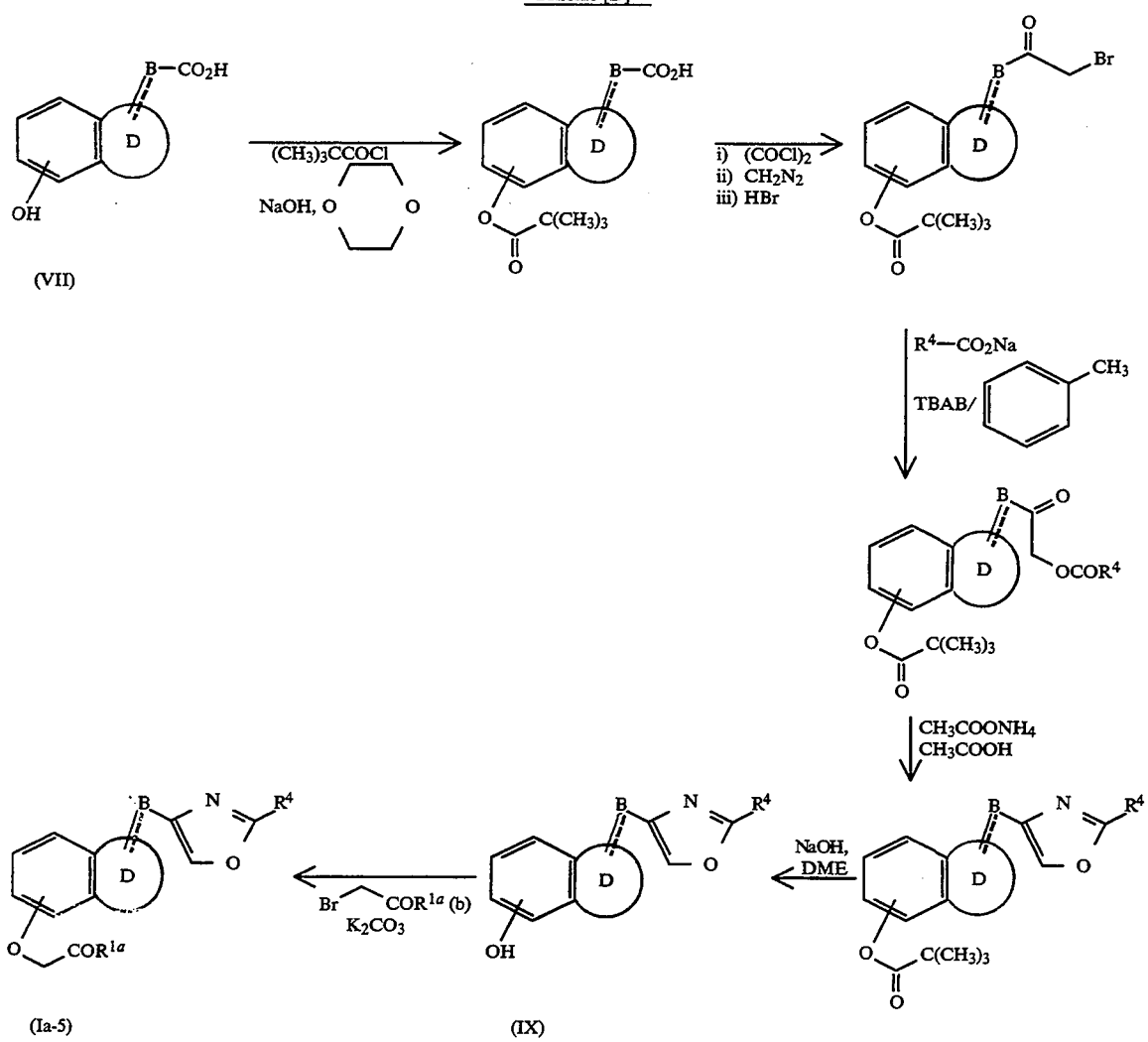
Scheme [E]
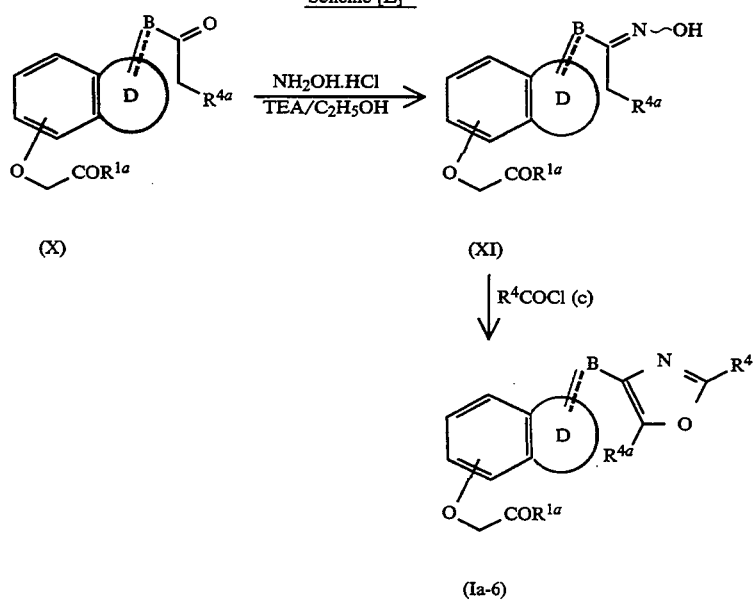

Scheme [F]
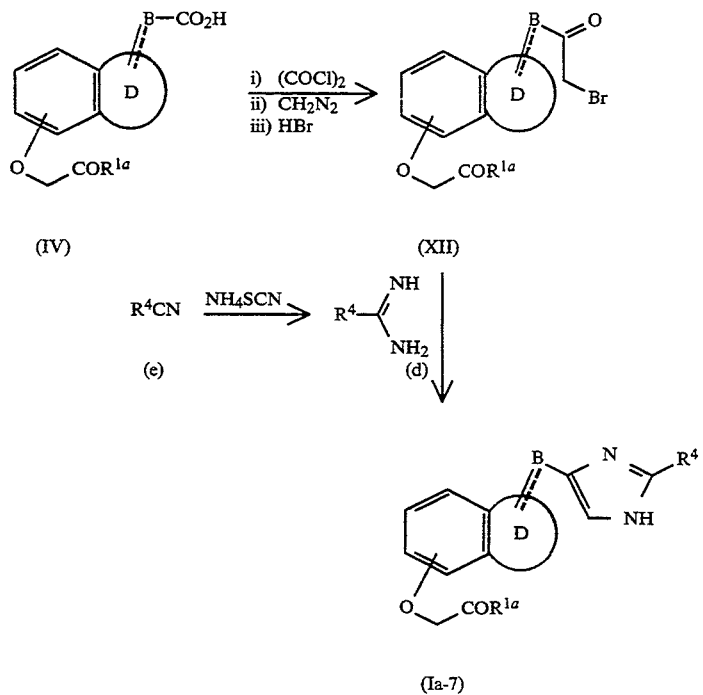
Scheme [G]
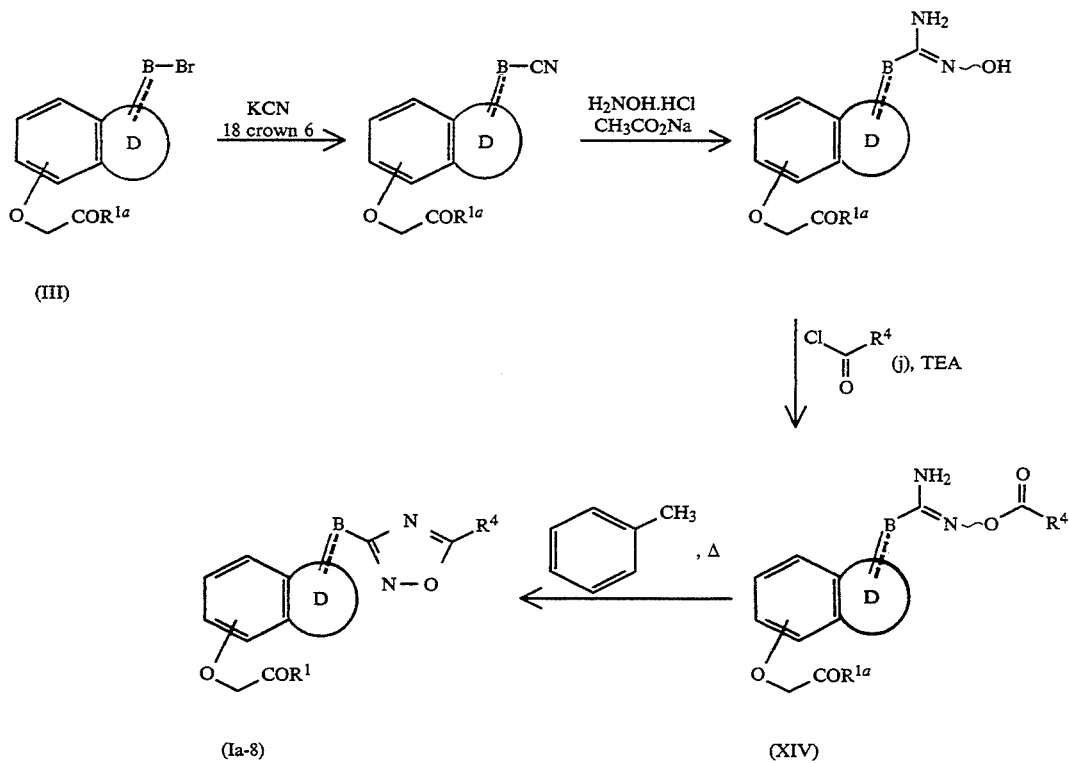

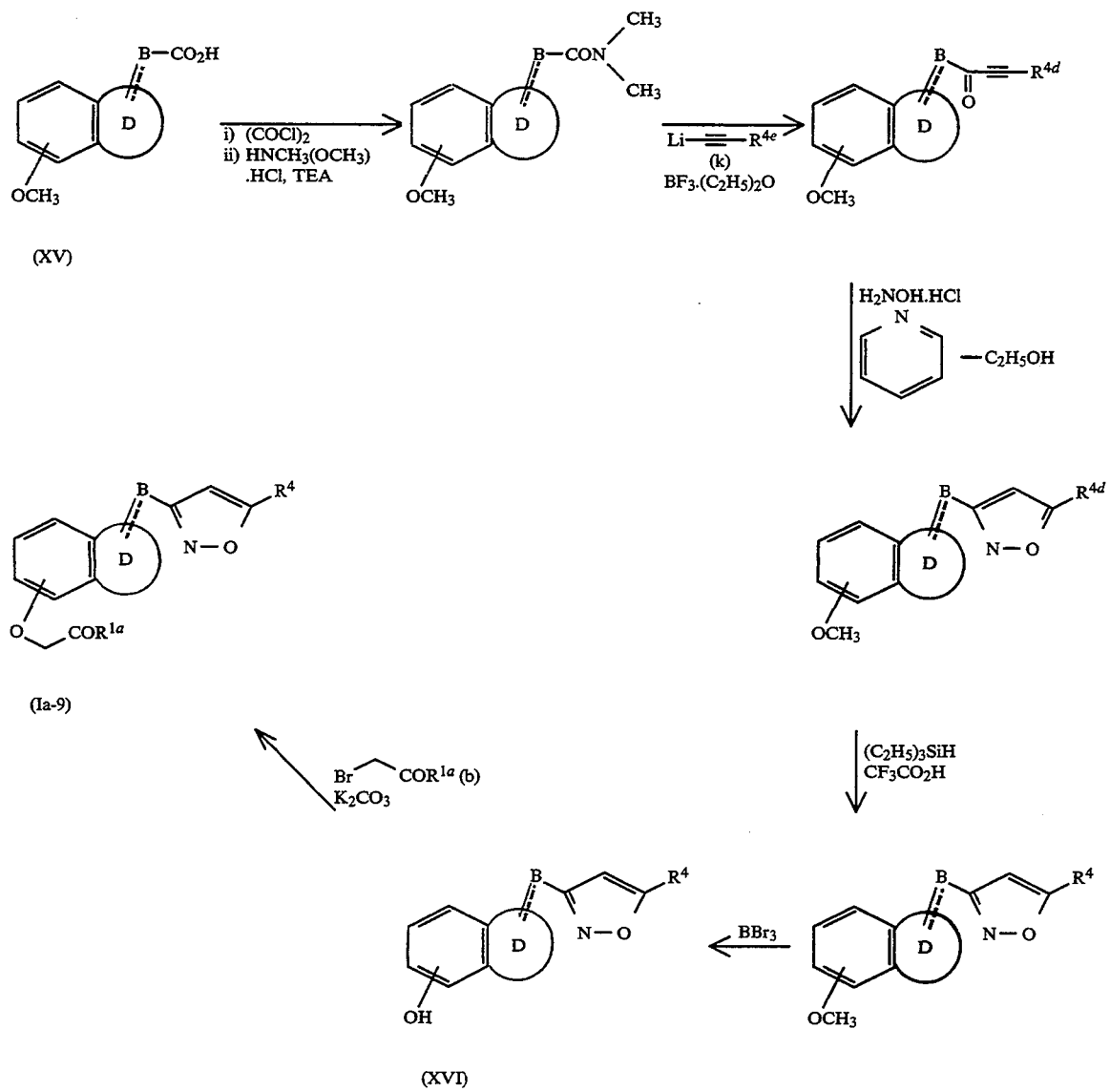
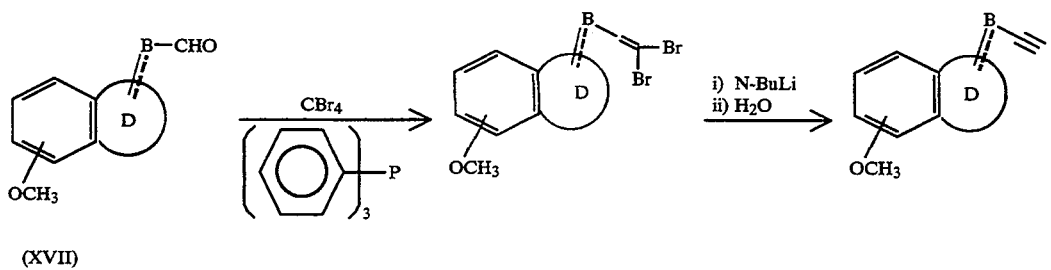

-continued
Scheme [I]
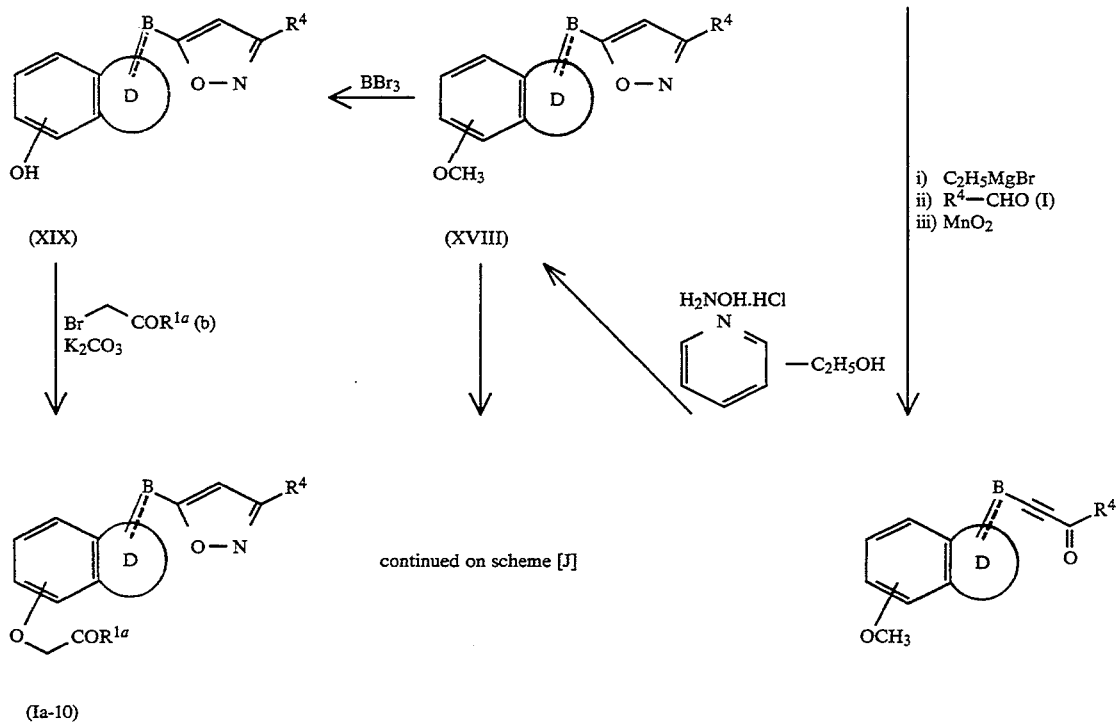
continued on scheme [J]
Scheme [J]
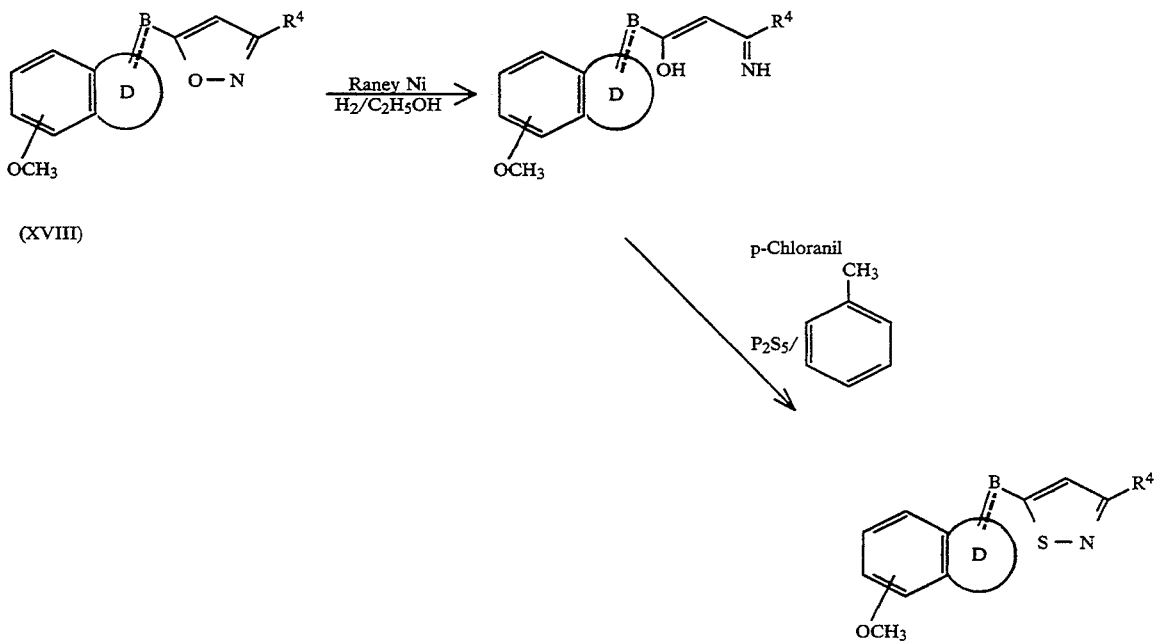

-continued
Scheme [J]
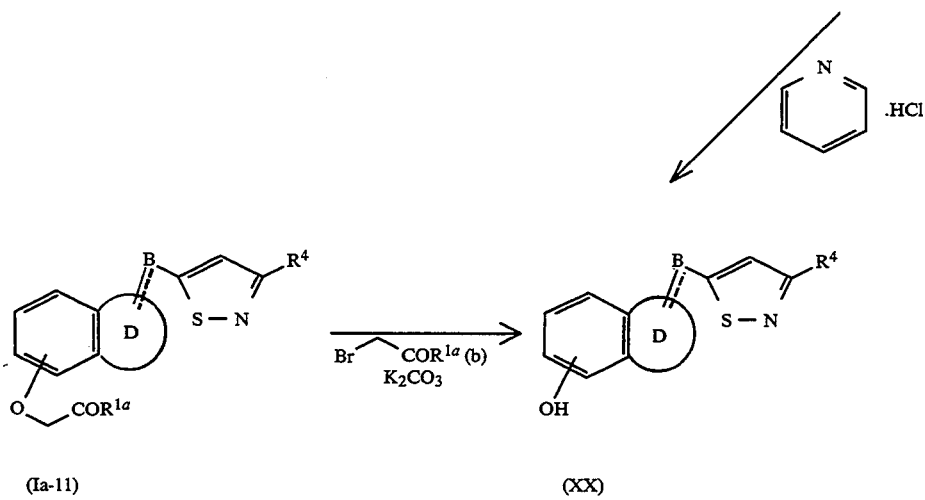
Scheme [K]
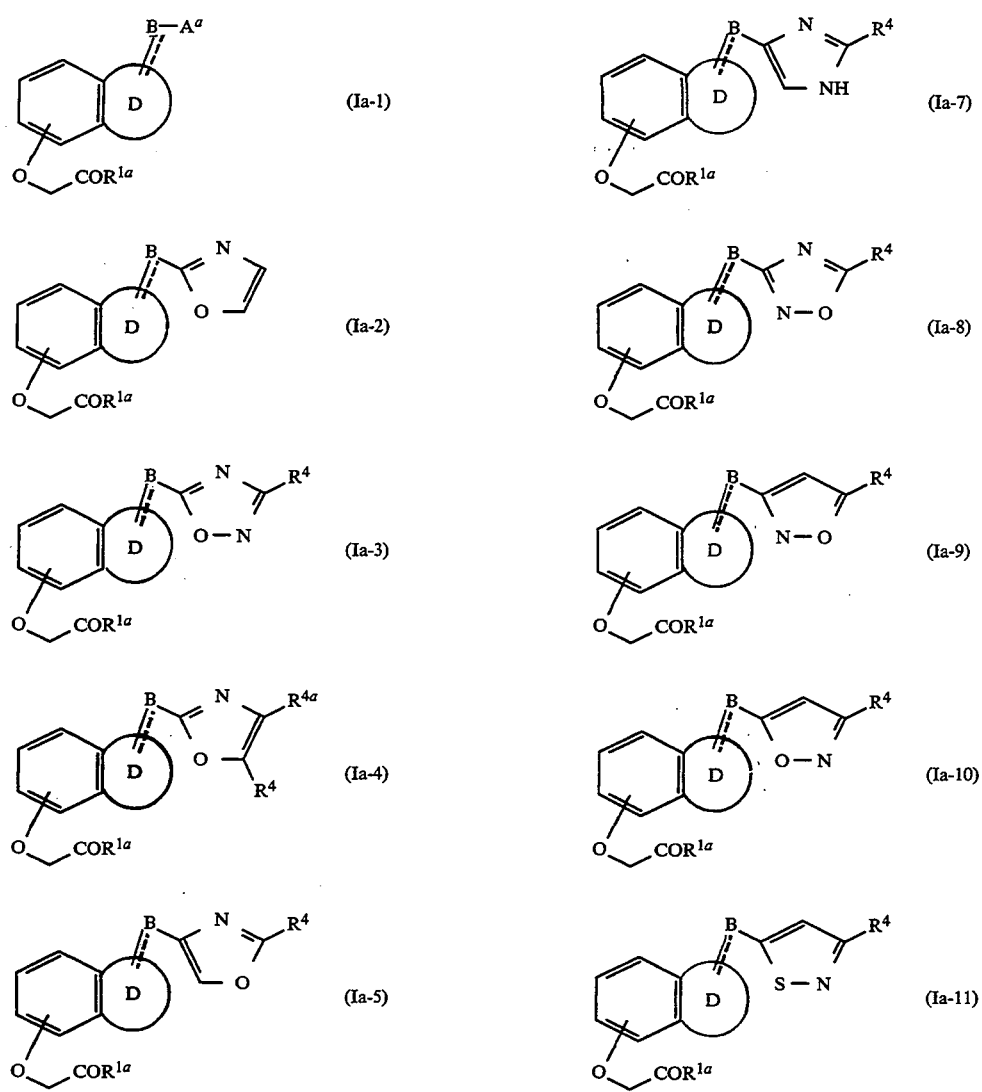

-continued
Scheme [K]

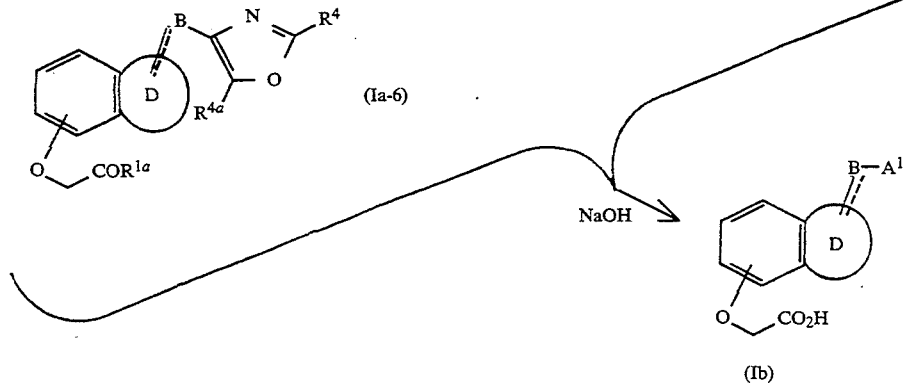

In the scheme,
$R^{4d}$ is
  (i) hydrogen atom,
  (ii) $C_{1-4}$ alkyl,
  (iii) phenyl or
  (iv) $C_{1-4}$ alkyl substituted by one or two rings optionally selected from 4-7 membered monocyclic hetero ring containing one or two nitrogen atom or phenyl and/or one hydroxy;

$R^{4e}$ is the same meaning as $R^{4d}$ provided that the hydroxy in $R^{4d}$ should be replaced by —OLi;

DMF is N, N-dimethylformamide;
TEA is triethylamine;
DHP is dihydropyran;
THP is tetrahydropyran-2-yl;
DME is dimethoxyethane;
TBAB is tetra-n-butylammonium bromide; and the other symbols are the same meaning as hereinbefore defined.

The compounds of the formulae (j), (k) and (l) are well known per se, and may be obtained commercially as reagents or may be prepared by methods known per se from commercially available reagents.

(2) In the compound of the present invention, of the formula (I), compounds of the formula (I-2);

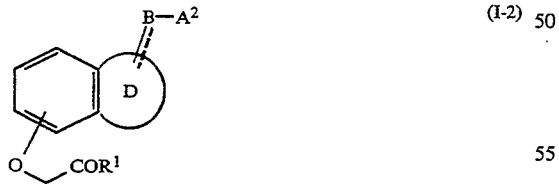 (I-2)

wherein $A^2$ is

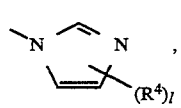 (i)

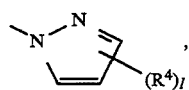 (iv)

-continued

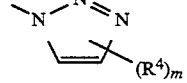 (v)

or

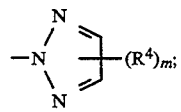 (vi)

wherein $R^4$ is the same meaning as hereinbefore defined, with the proviso that, a hetero ring as a substituent of $C_{1-4}$ alkyl should be bonded to the alkyl via a nitrogen atom in the hetero ring, and at least one group in $R^4$ is the alkyl substituted by a hetero ring, and the other symbols are the same meaning as hereinbefore defined, may be prepared:

(A) by subjecting a compounds of the formula (XIII):

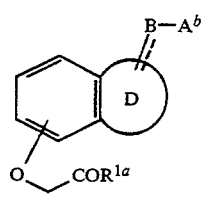 (XIII)

wherein $A^b$ is

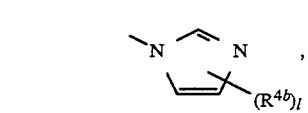 (i)

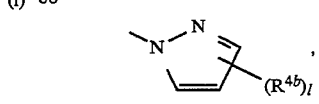 (iv)

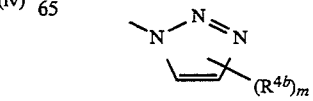 (v)

-continued or

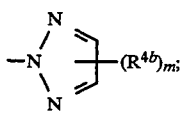

wherein $R^{4b}$ each independently, is
(i) hydrogen atom,
(ii) $C_{1-4}$ alkyl,
(iii) phenyl,
(iv) $C_{1-4}$ alkyl substituted by one or two of phenyl or ketone, the said phenyl may be also substituted by $C_{1-4}$ alkyl, $C_{1-4}$ alkoxy, halogen atom, nitro or trihalomethyl, when $R^{4b}$ is phenyl or the group containing phenyl;
at least one in $R^{4b}$ is $C_{1-4}$ alkyl substituted by ketone and the other symbols are the same meaning as hereinbefore defined, to a series of reactions of (1) hydrolysis→(2) reduction→(3) esterification→(if desired (4) mesylation)→(5) reaction with a compound of the formula (i):

$R^{4c}$       (i)

wherein $R^{4c}$ is 4–7 membered monocyclic hetero ring containing one or two nitrogen atom, or haloid acid thereof, (B) by subjecting a compound of the formula (Ic):

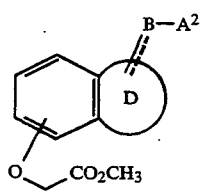

wherein all the symbols are the same meaning as hereinbefore defined, to the same procedure as method hereinbefore described in (L), (M) or (N) for the preparation of the compound of the formula (I-1) from those of formula (Ia) or (Ib).

The reaction (5) in (A) carried out in an appropriate organic solvent (e.q., dimethylformamide) at 110° C.

The compounds of the formulae (XIII) and (Ic) may be prepared by using a series of reactions depicted in the following scheme.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Starting materials and each reagents in the present specification are well known per se, or may be prepared by methods known per se.

For example, the processes for the preparation of the compounds of the formula:

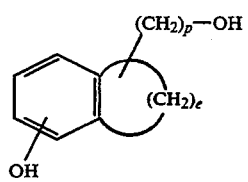

in the compounds of the formula (II), the compounds of the formula:

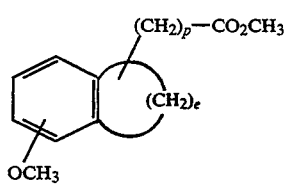

in the compounds of the formula (VI), the compounds of the formula:

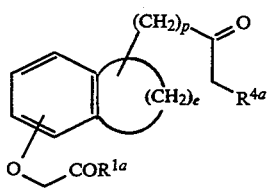

in the compounds of the formula (X) and the compounds of the formula:

Scheme [L]

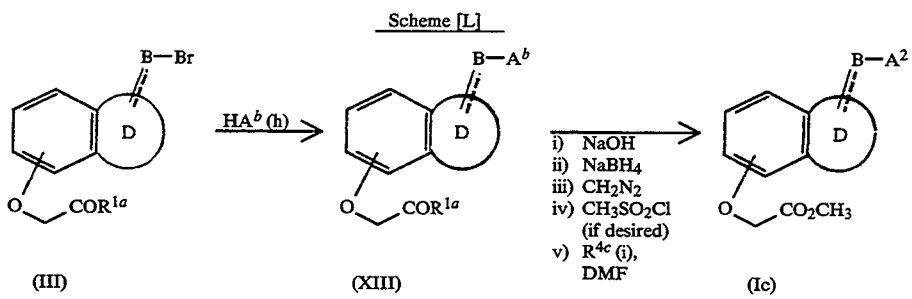

In the scheme, all the symbols are the same meaning as hereinbefore defined, and the compounds of the formulae (h) and (i) are well known per se, or may be prepared by methods known per se.

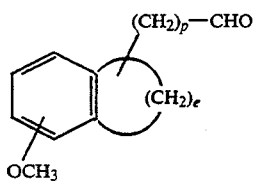

in the compound of the formula (XVII) are described in the specification of the Japanese Patent Application No. 3-130467.

The process for the preparation of the compounds of the formula:

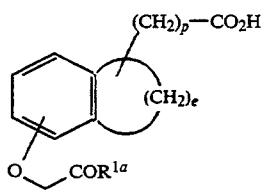

in the compounds of the formula(VI) is described in the specification of the Japanese Patent Application No. 3-322612.

The compounds of the formula (XV) may be prepared by methods known per se from the compound of the formula (IV) in described above.

Pharmacological Activities

It has been confirmed that the compounds of the present invention of the formula (I) possess an agonistic activity on $PGI_2$ receptor by the following experimental results.

i) Inhibitory activity on binding of $^3H$-iloprost to $PGI_2$ receptor on human blood platelet membrane fraction Method 50 mM Tris-HCl buffer (pH 7.4) containing 15 mM $MgCl_2$, 5 mM EDTA and 10 nM [$^3H$]-iloprost were used as reaction medium. To 0.2 ml of the reaction medium, human blood platelet membrane fraction (0.3 mg protein) was added with or without a test compound. The mixture was incubated at 24° C. for 30 min. After incubation, 4 ml of ice-cold 10 mM Tris-HCl buffer (pH 7.4) was added to the reaction mixture, and filtered through Whatman GF/B glass fiber filter, and washed 4 times with 4 ml of ice-cold 10 mM Tris-HCl buffer (pH 7.4) to separate bound and free [$^3H$]-iloprost. After washing, the filter was dried and radioactivity was counted. Non-specific binding was obtained by performing parallel binding experiments in the presence of 10 μM non-labelled iloprost. Specific binding was calculated by subtracting the non-specific binding from the total binding.

The inhibitory effect of test compound was calculated from the following equation.

The percentage of inhibition (%)=100−($B_1/B_0$×100)

$B_1$: specific [$^3H$]-iloprost binding in presence of test compound $B_0$: specific [$^3H$]-iloprost binding in absence of test compound The results are shown in the following table 1.

| EX. No. | IC$_{50}$ (μM) |
|---|---|
| 2 | 0.043 |

-continued

| EX. No. | IC$_{50}$ (μM) |
|---|---|
| 2(a) | 2.3 |
| 2(c) | 3.9 |
| 2(d) | 6.8 |
| 2(e) | 2.6 |
| 2(g) | 0.35 |
| 2(h) | 0.36 |
| 2(i) | 0.21 |
| 4(b) | 5.0 |
| 4(c) | 8.2 |
| 4(f) | 1.4 |
| 6 | 5.0 |
| 6(b) | 4.0 |
| 6(c) | 0.058 |
| 8 | 2.0 |
| 8(a) | 0.26 |
| 10 | 1.8 |
| 12 | 0.32 |
| 14 | 0.94 |
| 16 | 6.8 |
| 22 | 0.018 |
| 22(a) | 0.16 |
| 24 | 8.0 | ii) inhibitory effect on human blood platelet aggregation

Method

Platelet-rich plasma (PRP) was prepared from human blood (5×10$^5$ platelets/mm$^3$), and a test compound was added to PRP 1 min prior to the addition of ADP (4 μm). The aggregation was monitored using a platelet aggregometer (NBS HEMA TRACER 601, Niko Bioscience, Japan). The results are shown in the following table 2.

TABLE 2

| EX. No. | IC$_{50}$ (μM) |
|---|---|
| 2 | 0.045 |
| 2(a) | 13 |
| 2(c) | 12 |
| 2(d) | 20 |
| 2(e) | 15 |
| 2(g) | 0.30 |
| 2(i) | 0.15 |
| 4(b) | 11 |
| 6(b) | 16 |
| 8(a) | 1.0 |
| 10 | 5.1 |
| 12 | 1.0 |
| 14 | 1.6 |
| 16 | 12 |
| 22 | 0.093 |

Toxicity

The toxicity of the compounds of the present invention, of the formula (I) is very low and therefore, it may be confirmed that the compounds of the present invention are fully safe for pharmaceutical use.

Application for Pharmaceuticals

The compounds of the present invention, of the formula (I) possess an agonistic activity on $PGI_2$ receptor, and therefore are useful for the prevention and/or the treatment of thrombosis, arteriosclerosis, ischemic heart diseases, gastric ulcer and hypertension, etc.

For the purpose above described, the compounds of the formula (I), of the present invention, non-toxic salts thereof, acid additional salts thereof and hydrates thereof may be normally administered systemically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 100 μg and 100 mg, by parenteral administration up to several times per day, or continuous administration between 1 and 24 hrs. per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as lactose, etc.), and assisting agents for dissolving (such as glutamic acid, asparaginic acid etc.).

The tablets or pills may, if desired, be coated with a film of gastric or enteric material (such as sugar, gelatin, hydroxypropyl cellulose or hydroxypropylmethyl cellulose phthalate etc.), or be coated with more than two films. And further, coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (purified water, ethanol etc.). Besides inert diluents, such compositions may also comprise adjuvants (such as wetting agents, suspending agents, etc.), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. No. 2,868,691 or 3,095,355 (herein incorporated in their entireties by reference) may be used.

Injections for parenteral administration include sterile aqueous or non-aqueous solutions, suspensions and emulsions. In such compositions, one more of active compound(s) is or are admixed with at least one of inert aqueous diluent(s) (distilled water for injection, physiological salt solution etc.) or inert non-aqueous diluent(s) (propylene glycol, polyethylene glycol, olive oil, ethanol, POLYSORBATE80 (registered trade mark)etc.).

Injections may comprise additional other than inert diluents: e.g. preserving agents, wetting agents, emulsifying agents, dispersing agents, stabilizing agent (lactose etc.), assisting agents such as assisting agents for dissolving (glutamic acid, asparaginic acid etc.).

They may be sterilized for example, by filtration through a bacteria-retaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

Other compositions for parenteral administration include liquids for external use, and endermic liniments, ointment, suppositories and pessaries which comprise one or more of the active compound(s) and may be prepared by per se known methods.

REFERENCE EXAMPLE AND EXAMPLES

The following reference examples and examples are intended to illustrate, but not limit, the present invention.

The solvents in parentheses show the developing or eluting solvents and the ratios of the solvents used are by volume in chromatographic separations.

Unless otherwise specified, "IR" was measured by KBr method, "NMR" was measured in a solution of CDCl$_3$, "mp." means melting point, and "MS" means mass spectrum.

Reference example 1

Methyl (2-bromomethyl-1,2,3,4-tetrahydronaphthalen-5-yloxy) acetate Reference example 1

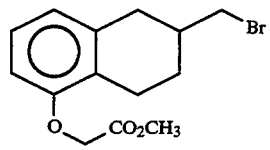

To a solution of methyl (2-hydroxymethyl-1,2,3,4-tetrahydronaphthalen-5-yloxy) acetate (4.19 g) in methylene chloride (80 ml) were successively added triphenylphosphine (6.61 g) and carbon tetrabromide (11.1 g) at room temperature. The mixture was concentrated under reduced pressure. The residue was purified by silica gel column chromatography (n-hexane:ethyl acetate=9:1) to give the title compound (4.58 g) having the following physical data.

IR(cm$^{-1}$): ν2927, 2849, 1762, 1605, 1586, 1467, 1437, 1376, 1345, 1283, 1206, 1120, 1003, 766, 710.

Reference example 2

1-Benzyl-4-ethoxycarbonylpyrazole

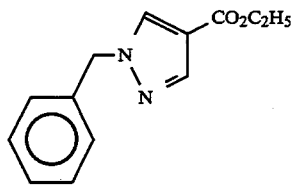

To a suspension of sodium hydride (containing 63%, 652 mg) in dimethylformamide (abbreviated as DMF hereinafter) was added a solution of 4-ethoxycarbonylpyrazole (2.00 g) in DMF (15 ml) at room temperature.

After stirred for 30 min at room temperature, to the mixture was added benzylbromide (2.04 ml). After stirred for 30 min, the mixture was quenched by addition of water. The mixture was extracted with ethyl acetate-n-hexane. The extract was washed with a saturated aqueous solution of sodium chloride, dried over anhydrous magnesium sulfate, and evaporated. The residue was purified by silica gel column chromatography (n-hexane:ethyl acetate=3:1) to give the title compound (2.98 g) having the following physical data.

TLC: Rf 0.27(ethyl acetate:n-hexane=1:3); IR (cm$^{-1}$): ν3122, 2973, 1714, 1555, 1457, 1373, 1350, 1307, 1224, 1192, 1115, 1027, 988, 881, 771, 706, 621.

Reference example 3

1-Benzyl-4-diphenylhydroxymethylpyrazole

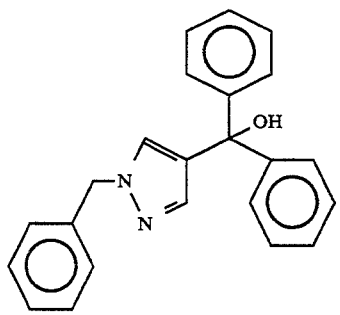

To a solution of the compound prepared in reference example 2 (2.85 g) in tetrahydrofuran (THF, 30 ml) was added phenylmagnesium bromide (61.9 m mol) at 0° C. After stirred for 1 h at room temperature, the mixture was quenched by addition of ice and an aqueous solution of ammonium chloride. The mixture was extracted with ethyl acetate-n-hexane (1:2). The extract was washed with water and a saturated aqueous solution of sodium chloride, successively, dried over anhydrous magnesium sulfate, and evaporated. The residue was purified by silica gel column chromatography (ethyl acetate:n-hexane=2:5) to give the title compound (1.31 g) having the following physical data.

TLC: Rf 0.48 (ethyl acetate:n-hexane=1:1); IR (cm$^{-1}$): ν3242, 3062, 3030, 2929, 1601, 1553, 1495, 1449, 1387, 1332, 1160, 1030, 1001, 879, 808, 757, 729, 700, 529.

Reference example 4

4-Diphenylmethylpyrazole

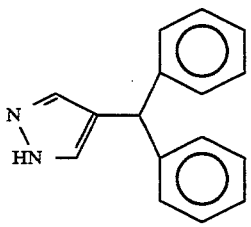

To a mixture of small piece of sodium (1.5 g) in liquid ammonia (30 ml) was added a solution of the compound prepared in reference example 3 (1.3 g) in THF (10 ml) at −78° C. The mixture was stirred at −70° C. in the beginning, and the temperature of the mixture was raised gradually to −25° C. over 3 h. The mixture was quenched by addition of ammonium chloride (1.5 g).

The mixture was warm up to room temperature and excess ammonia was removed. The residue was diluted with water, and extracted with ethyl acetate. The extract was washed with a saturated aqueous solution of sodium chloride, dried over anhydrous magnesium sulfate, and evaporated. The residue was purified by silica gel column chromatography (ethyl acetate:n-hexane=2:1→1:0) to give the title compound having the following physical data.

TLC: Rf 0.40 (ethyl acetate:n-hexane=1:1); IR (cm$^{-1}$): ν3120, 3024, 2946, 1601, 1490, 1451, 1391, 1362, 1144, 1078, 1052, 1032, 1007, 953, 879, 824, 750, 734, 699, 663, 636, 506, 476.

Reference example 5

1.1-Diphenyl-2-amino-hydroxyiminoethane

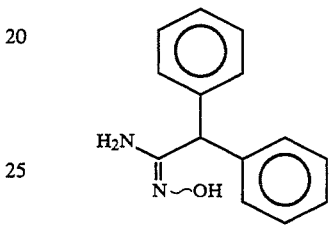

A mixture of diphenylacetonitrile (7.0 g), hydroxylamine hydrochloride (3.03 g), and sodium acetate (6.67 g) in 150 ml of 5:1 ethanol-water was refluxed for 4 h. The mixture was concentrated under reduced pressure. The residue was triturated with water, filtrated, and dried to give the title compound (2.5 g) having the following physical data.

NMR: δ7.40-7.00 (10H, m), 5.55 (2H, brs), 4.88 (1H, s), 4.57 (1H, brs); IR (cm$^{-1}$): ν3481, 3371, 3196, 1668, 1575, 1492, 1452, 1359, 1084, 1030, 959, 933, 863, 725, 704, 633.

Reference example 6

Methyl[1-[2-(1-amino-2,2-diphenylethylidene)aminoxycarbonylethyl]-1,2,3,4-tetrahydronaphthalen-5-yloxy-]acetate

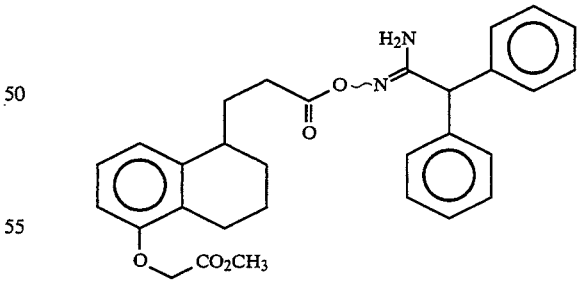

A stirred suspension of 3-(5-methoxycarbonylmethoxy-1,2,3,4-tetrahydronaphthalen-1-yl)propionic acid (300 mg) and oxalyl chloride (5.0 ml) was refluxed for 1 h. The mixture was cooled to room temperature and concentrated under reduced pressure. The residue was dissolved into methylene chloride (10 ml). The solution was added dropwise to an ice bath-cooled solution of 1,1-diphenyl-2-amino-2-(hydroxyimino)ethane (279 mg) prepared in reference example 5 and triethylamine (0.29 ml) in methylene chloride (3.0 ml). After the addition of the solution was completed, the mixture was stirred for 1 h at room temperature. The mixture was diluted with ethyl acetate. The extract was washed with water, dried over anhydrous magnesium sulfate, and evaporated. The residue was purified by silica gel column chromatography (n-hexane:ethyl acetate=3:2) to give the title compound (447 mg) having the following physical data.

MS(m/z): 501 (M++1); IR (cm$^{-1}$): ν3493, 3370, 2944, 1737, 1617, 1581, 1494, 1456, 1367, 1338, 1274, 1164, 1130, 1081, 1003, 872, 783, 702, 640.

Reference example 7

2-Carboxymethyl-5-hydroxy-1,2,3,4-tetrahydronaphthalene

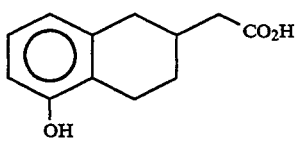

A mixture of 2-methoxycarbonylmethyl-5-methoxy-1,2,3,4-tetrahydronaphthalene (4.0 g) and pyridine hydrochloride (40 g) was stirred for 2 h at 190° C. The mixture was cooled to room temperature, dissolved into water. The mixture was extracted with ethyl acetate. The extract was washed with a saturated aqueous solution of sodium chloride, dried over anhydrous magnesium sulfate, and evaporated to give the title compound having the following physical data. The obtained residue was used for the next step without purification.

NMR: δ8.38 (1H, brs), 6.92 (1H, t, J=8 Hz), 6.64 (1H, d, J=8 Hz), 6.57 (1H, d, J=8 Hz), 2.98–2.78 (2H, m), 2.67–1.91 (7H, m), 1.54–1.30 (1H, m).

Reference example 8

2-Methoxycarbonylmethyl-5-hydroxy-1,2,3,4-tetrahydronaphthalene

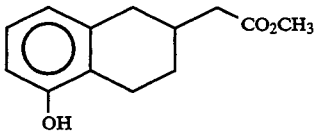

To a solution of thionyl chloride (5.0 ml) was added dropwise methanol (18 ml) at −20° C. The mixture was stirred for 30 min at −20° C. To the mixture was added a solution of the residue prepared in reference example 7 in methanol at −20° C. After stirred for 1 h at room temperature, the mixture was concentrated under reduced pressure. The residue was purified by silica gel column chromatography (n-hexane:ethyl acetate=4:1) to give the title compound (3.52 g) having the following physical data.

TLC: Rf 0.22 (n-hexane:ethyl acetate=3:1); IR (cm$^{-1}$): ν3425, 2925, 1713, 1587, 1466, 1439, 1336, 1279, 1159, 1088, 1070, 1010, 772, 713.

Reference example 9

2-Methoxycarbonylmethyl-5-(tetrahydropyran-2-yl)oxy-1,2,3,4-tetrahydronaphthalene

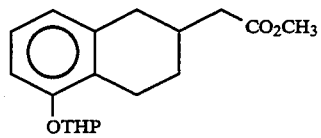

A mixture of the compound prepared in reference example 8 (1.25 g), dihydropyran (0.68 ml), a catalytic amount of pyridinum p-toluenesulfonic acid and methylene chloride (10 ml) was stirred for 3 days at room temperature. After adding of triethylamine (0.5 ml), the mixture was concentrated under reduced pressure. The residue was purified by silica gel column chromatography (n-hexane:ethyl acetate=6:1) to give the title compound (1.72 g) having the following physical data.

IR(cm$^{-1}$): ν2943, 1738, 1586, 1464, 1438, 1356, 1283, 1251, 1202, 1158, 1124, 1076, 1024, 955, 918, 873, 820, 770, 736.

Reference example 10

[5-(Tetrahydropyran-2-yl)oxy-1,2,3,4-tetrahydronaphthalen-2-yl]acetic acid

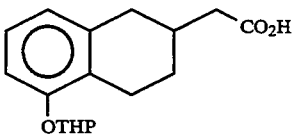

To a solution of the compound prepared in reference example 9 (1.72 g) in dimethoxyethane (15 ml) was added 2N aqueous solution of sodium hydroxide (5.6 ml) at 0° C. This solution was stirred overnight at room temperature. After neutralized by addition of 2N hydrochloric acid (5.6 ml), the mixture was extracted with ethyl acetate. The extract was washed with water and a saturated aqueous solution of sodium chloride, successively, dried over anhydrous magnesium sulfate, and evaporated. The residue was recrystallized from n-hexane-ethyl acetate to give the title compound (1.27 g) having the following physical data.

mp.: 104°~109° C.; MS(m/z): 290 (M+), 256, 234.

Reference example 11

2-Diphenylmethylcarbonylmethoxycarbonylmethyl-5-(tetrahydropyran-2-yl)oxy-1,2,3,4-tetrahydronaphthalene

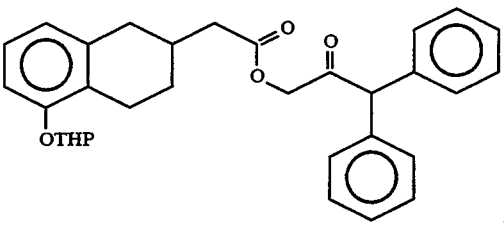

To a solution of the compound prepared in reference example 10 (290 mg) in ethanol (2 ml) was added 1N aqueous solution of sodium hydroxide (1 ml). The solution was concentrated under reduced pressure to give sodium salt of the compound prepared in reference example 10. A mixture of sodium salt thus obtained, tetra-n-butylammonium bromide (32 mg) and 3-bromo-1,1-diphenyl-2-propanone (578 mg) in toluene (5.0 ml) was stirred overnight at room temperature. The mixture was poured into water, and was extracted with ether. The extract was washed with water and a saturated aqueous solution of sodium chloride, successively, dried over anhydrous magnesium sulfate, and evaporated. The residue was purified by silica gel column chromatography (n-hexane:ethyl acetate=5:1) to give the title compound (447 mg) having the following physical data.

TLC: Rf 0.45 (n-hexane:ethyl acetate=3:1); IR(cm$^{-1}$): $\nu$3029, 2938, 1735, 1585, 1499, 1464, 1412, 1358, 1251, 1202, 1155, 1123, 1078, 1024, 955, 918, 900, 873, 820, 771, 747, 703.

Reference example 12

2-(4-Diphenylmethyloxazol-2-yl)methyl-5-hydroxy-1,2,3,4-tetrahydronaphthalene

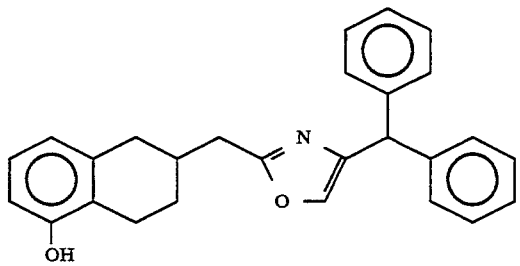

A mixture of the compound prepared in reference example 11 (386 mg), ammonium acetate (298 mg) and acetic acid (2.0 ml) was refluxed for 2.5 h. The mixture was diluted with ether. The mixture was washed with an aqueous solution of potassium carbonate, water and a saturated aqueous solution of sodium chloride, successively, dried over anhydrous magnesium sulfate, and evaporated. The residue was purified by silica gel column chromatography (ethyl acetate:n-hexane=1:4) to give the title compound (147 mg) having the following physical data.

TLC: Rf 0.45 (ethyl acetate:n-hexane=1:2); IR(cm$^{-1}$): $\nu$3061, 3028, 2924, 2362, 1736, 1587, 1571, 1495, 1465, 1453, 1435, 1338, 1307, 1247, 1202, 1156, 1123, 1099, 1032, 995, 956, 904, 836, 770, 749, 701, 507.

Reference example 13

(5-tert-butylcarbonyloxy-1,2,3,4-tetrahydronaphthalen-2-yl)acetic acid

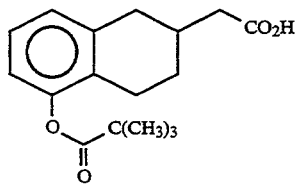

To a mixture of the compound prepared in reference example 7 (600 mg), 2N aqueous solution of sodium hydroxide (2.91 ml) and dioxane (3.0 ml) was added pivaloyl chloride (0.39 ml) at 0° C. The mixture was stirred for 3 h at room temperature. After quenched by addition of 2N hydrochloric acid, the mixture was extracted with ethyl acetate. The extract was washed with a saturated aqueous solution of sodium chloride, dried over anhydrous magnesium sulfate, and evaporated. The residue was purified by silica gel column chromatography (chloroform:methanol=19:1) to give the title compound (408 mg) having the following physical data.

TLC: Rf 0.43 (methanol:chloroform=1:9); IR (cm$^{-1}$): $\nu$2975, 2932, 1751, 1708, 1582, 1482, 1461, 1413, 1368, 1282, 1236, 1125, 1032, 941, 767, 712.

Reference example 14

2-Bromomethylcarbonylmethyl-5-tert-butylcarbonyloxy-1,2,3,4-tetrahydronaphthalene

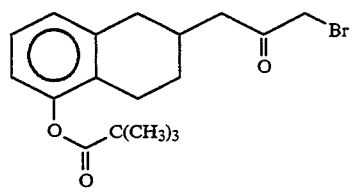

To a mixture of the compound prepared in reference example 13 (390 mg) and trace amount of DMF was added oxalyl chloride (4.0 ml) at room temperature. The mixture was stirred for 1.5 h at room temperature. The mixture was concentrated under reduced pressure to remove excess oxalyl chloride and the residue was diluted with ether. This solution was added to an ethereal solution of diazomethane (20 ml) at 0° C. and the mixture was stirred for 2 h at 0° C. Gaseous hydrogen bromide (prepared from tetraline and bromine) was bubbled into the mixture for a period of 20 min at 0° C. After adding of water, the organic layer was separated. The organic layer was washed with water and a saturated aqueous solution of sodium chloride, successively, dried over anhydrous magnesium sulfate, and evaporated to give the title compound (424 mg) having the following physical data.

TLC: Rf 0.22 (n-hexane:ethyl acetate:=7:1); IR (cm$^{-1}$): $\nu$2974, 2932, 1747, 1581, 1479, 1460, 1397, 1364, 1280, 1236, 1127, 1032, 983, 898, 768, 711.

Reference example 15

2-Diphenylmethylcarbonyloxymethylcarbonylmethyl-5-tert-butylcarbonyloxy-1,2,3,4-tetrahydronaphthalene

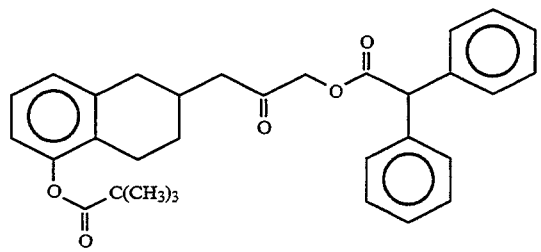

A mixture of sodium diphenylacetate (1.67 mmol), tetra-n-butylammonium bromide (32 mg), the compound prepared in reference example 14 (400 mg) and toluene (5.0 ml) was stirred overnight at room temperature. The mixture was poured into water and the mixture was extracted with ether. The extract was washed with water and a saturated aqueous solution of sodium chloride, successively, dried over anhydrous magnesium sulfate, and evaporated. The residue was purified by silica gel column chromatography (n-hexane:ethyl acetate=5:1) to give the title compound (531 mg) having the following physical data.

TLC: Rf 0.40 (n-hexane:ethyl acetate:=3:1); IR (cm$^{-1}$): ν3029, 2974, 2931, 1747, 1581, 1496, 1460, 1397, 1370, 1279, 1235, 1186, 1126, 899, 767, 746, 702.

Reference example 16

2-(2-Diphenylmethyloxazol-4-yl)methyl-5-hydroxy-1,2,3,4-tetrahydronaphthalene

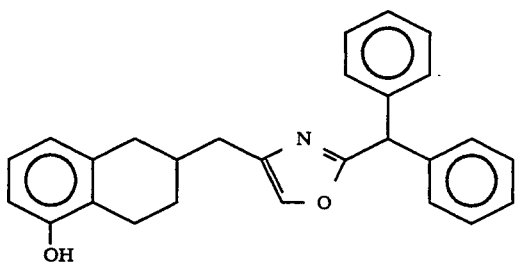

To a solution of the compound (190 mg) obtained by the same procedure as reference example 12, using the compound prepared in reference example 15, in dimethoxyethane (3.0 ml) and methanol (0.5 ml) was added 1N aqueous solution of sodium hydroxide (1.5 ml) at 0° C. The solution was stirred for 2 h at room temperature. After neutralized by addition of 1N hydrochloric acid (1.5 ml), the mixture was extracted with ether. The extract was washed with a saturated aqueous-solution of sodium bicarbonate and a saturated aqueous solution of sodium chloride, successively, dried over anhydrous magnesium sulfate, and evaporated. The residue was purified by silica gel column chromatography (n-hexane:ethyl acetate=3:1) to give the title compound (150 mg) having the following physical data.

TLC: Rf 0.25 (n-hexane:ethyl acetate:=3:1); IR (cm$^{-1}$): ν3062, 3029, 2921, 2844, 1735, 1587, 1557, 1495, 1464, 1338, 1275, 1202, 1158, 1091, 1032, 1004, 985, 846, 770, 751, 699, 640, 585, 506.

Reference example 17

Methyl [2-(2-hydroxyimino-n-pentyl)-1,2,3,4-tetrahydronaphthalen-5yloxy]acetate

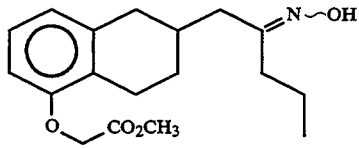

A mixture of methyl [2-(2-oxo-n-pentyl)-1,2,3,4-tetrahydronaphthalen-2yloxy]acetate (608 mg), hydroxyamine hydrochloride (290 mg), triethylamine (0.55 ml) and ethanol (5.0 ml) was stirred overnight at room temperature. After adding of triethylamine (1.0 ml), the mixture was concentrated under reduced pressure. The residue was dissolved into a mixture of ether and water. The organic layer was separated and was washed with water and a saturated aqueous solution of sodium chloride, successively, dried over anhydrous magnesium sulfate, and evaporated. The residue was purified by silica gel column chromatography (n-hexane:ethyl acetate=2:1) to give the title compound (540 mg) having the following physical data.

mp.: 95.9°~97° C.; TLC: Rf 0.24 (n-hexane:ethyl acetate:=3:1); IR (cm$^{-1}$): ν3246, 2942, 1767, 1586, 1468, 1436, 1347, 1311, 1276, 1200, 1195, 1127, 1003, 963, 948, 828, 766, 744, 709.

Reference example 18

Methyl [2-(3-bromo-2-oxopropyl)-1,2,3,4-tetrahydronaphthalen-5-yloxy]acetate

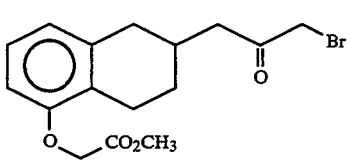

By the same procedure as reference example 14, using (5-methoxycarbonylmethoxy-1,2,3,4-tetrahydronaphthalene-2-yl) acetic acid, the title compound having the following physical data was given.

mp.: 77°~78° C.; TLC: Rf 0.25 (n-hexane:ethyl acetate:=4:1); IR (cm$^{-1}$): ν3010, 2944, 2920, 2905, 1763, 1735, 1583, 1469, 1435, 1398, 1384, 1343, 1264, 1218, 1205, 1149, 1101, 1088, 1030, 966, 777, 745, 710, 608.

Reference example 19

A mixture of amidinodiphenylmethane (A) and amidinodiphenylhydroxymethane (B)

(A)

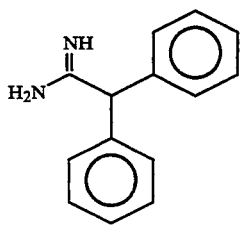

or (B)

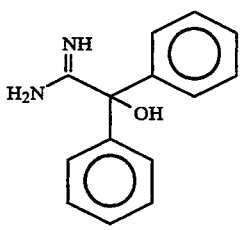

A mixture of diphenylacetonitrile (10 g) and ammonium thioisocyanate (16 g) was stirred for 5 h at 180° C. The mixture was cooled and quenched by addition of hot water. The mixture was filtrated and to the filtrate was added 5N aqueous solution of sodium hydroxide. The mixture was extracted with chloroform. The extract was dried over anhydrous sodium sulfate, and evaporated. The residue was treated with picric acid (1.5 g) and ethanol (50 ml). The precipitate was filtrated, washed with ethanol and dissolved in aqueous solution of sodium hydroxide. This solution was extracted with chloroform. The extract was dried over anhydrous sodium sulfate, and evaporated to give a mixture of title compounds having the following physical data.

TLC:(A) Rf 0.45, (B) Rf 0.38 (chloroform:methanol:acetic acid=17:2:1); NMR: δ7.46–7.17 (10H, m), 4.94 (1H, s).

Reference example 20

Methyl [2-(4-benzoylpyrazol-1-yl)methyl-1,2,3,4-tetrahydronaphthalen-5-yloxy]acetate

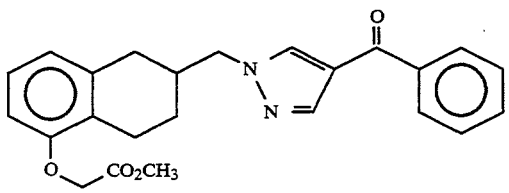

By the same procedure as a series of reactions of reference example 1→example 1, using 4-benzoylpyrazole instead of the compound prepared in reference example 4, the title compound having the following physical data was given.

TLC: Rf 0.43 (n-hexane:ethyl acetate:=1:1).

Reference example 21

Methyl [1-(2-cyanoethyl)-1,2,3,4-tetrahydronaphthalen-5-yloxy]acetate

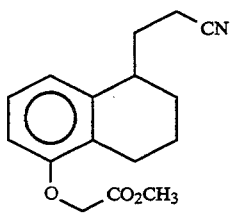

A mixture of potassium cyanide (1.16 g) and 18-Crown-6 (registered trade mark, 236 mg) in acetonitrile (18 ml) was stirred for 15 min under an atmosphere of argon. To the mixture was added a solution of methyl [1-(2-bromoethyl)-1,2,3,4-tetrahydronaphthalen-5-yloxy]acetate (2.92 g) and tributylphosphine (1.99 g) in acetonitrile (10 ml). To the mixture was added dropwise a solution of carbon tetrachloride (0.95 ml) in acetonitrile (10 ml) under cooling with ice. The mixture was stirred overnight at room temperature. The mixture was diluted with ether, and the mixture was washed with 10% aqueous solution of citric acid. To this solution was added carbon tetrachloride (10 ml), and washed with water and a saturated aqueous solution of sodium chloride, successively, dried over anhydrous magnesium sulfate, and evaporated. The residue was purified by silica gel column chromatography (n-hexane:ethyl acetate=1:9) to give the title compound (1.72 g) having the following physical data.

NMR: δ7.05 (1H, t, J=8 Hz), 6.83 (1H, d, J=8 Hz), 6.52 (1H, d, J=8 Hz), 2.90–2.60 (5H, m), 2.30–1.50 (6H, m).

Reference example 22

Methyl [1-(3-amino-3-hydroxyimino)propyl-1,2,3,4-tetrahydronaphthalen-5-yloxy]acetate

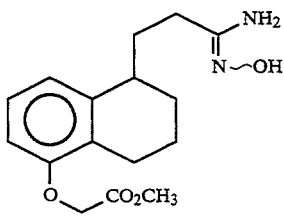

To a mixture of ethanol and water (5:1, 30 ml) were successively added the compound prepared in reference example 21 (1.01 g), hydroxyamine hydrochloride (331 mg) and sodium acetate (391 mg). The mixture was refluxed overnight. The mixture was concentrated under reduced pressure. The residue was purified by silica gel column chromatography (n-hexane:ethyl acetate=1:1) to give the title compound (132 mg) having the following physical data.

MS(m/z): 306 (M+ +1).

Reference example 23

Methyl [1-[3-(diphenylmethylcarbonyloxyimino)-3-aminopropyl]-1,2,3,4-tetrahydronaphthalen-5-yloxy]acetate

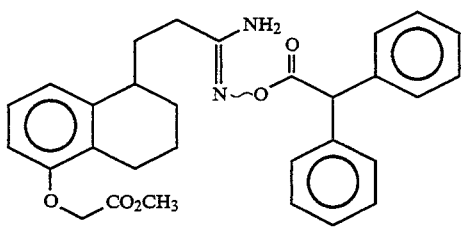

A suspension of diphenylacetic acid (201 mg) and thionyl chloride (5 ml) was refluxed for 1 h. The mixture was cooled to room temperature, and concentrated under reduced pressure. To a solution of the residue and the compound prepared in reference example 22 (132 mg) in methylene chloride (5 ml) was added triethylamine (0.27 ml). The mixture was stirred overnight at room temperature. After quenched by addition of water, the mixture was extracted with ether. The extract was washed with water and a saturated aqueous solution of sodium chloride, successively, dried over anhydrous magnesium sulfate, and evaporated. The residue was purified by silica gel column chromatography (n-hexane:ethyl acetate=1:1) to give the title compound (67 mg) having the following physical data.

MS(m/z): 501 (M+ +1).

Reference example 24

2-(N-Methoxy-N-methylcarbamoylmethyl)-5-methoxy-1,2,3,4-tetrahydronaphthalene

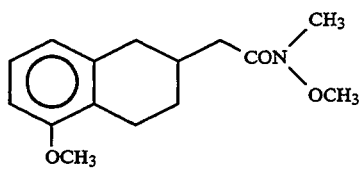

To a solution of 2-carboxymethyl-5-methoxy-1,2,3,4-tetrahydronaphthalene (10.1 g) in methylene chloride (20 ml) was added oxalyl chloride (30 ml) at 0° C. The mixture was stirred for 45 min at room temperature. The mixture was concentrated under reduced pressure, and the residue was dissolved into methylene chloride (50 ml). This solution was added to a solution of N, O-dimethyhydroxylamine hydrochloride (5.37 g), triethylamine (19.2 ml) and methylene chloride (150 ml) at 0° C. The mixture was stirred for 30 min at room temperature. After adding of 1N hydrochloric acid, the mixture was extracted with ethyl acetate. The extract was washed with water and a saturated aqueous solution of sodium chloride, successively, dried over anhydrous magnesium sulfate, and evaporated. The residue was purified by silica gel column chromatography (n-hexane:ethyl acetate=2:1) to give the title compound (10.88 g) having the following physical data.

MS(m/z): 263 (M+).

Reference example 25

2-(5-Hydroxy-5,5-diphenyl-2-oxo-3-pentynyl)-5-methoxy-1,2,3,4-tetrahydronaphthalene

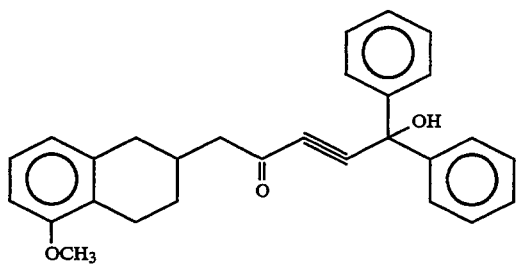

To a solution of 1,1-diphenyl-2-propyn-1-ol (2.15 g) in THF (20 ml) added dropwise n-butyllithium (13 ml, 1.6M/L in hexane solution) at −70° C. The mixture was stirred for 30 min at the same temperature. To the mixture was added boron trifluoride etherate (2.7 ml), and stirred for 30 min. To the mixture was added a solution of the compound prepared in reference example 24 (900 mg) in THF (10 ml) at −70° C., and stirred for 1 h. After quenched by addition of ammonium chloride, the mixture was extracted with ethyl acetate. The extract was washed with water and a saturated aqueous solution of sodium chloride, successively, dried over anhydrous magnesium sulfate, and evaporated. The residue was purified by silica gel column chromatography (n-hexane:ethyl acetate=7:1) to give the title compound (1.05 g) having the following physical data.

MS(m/z): 410 (M+).

Reference example 26

2-[5-(1,1-Diphenyl-1-hydroxymethyl)isoxazol-3-yl)methyl-5-methyoxy-1,2,3,4-tetrahydronaphthalene

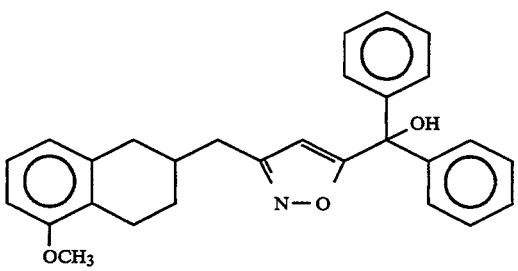

A mixture of the compound prepared in reference example 25 (820 mg), hydroxyamine hydrochloride (1.50 g), pyridine (10 ml) and ethanol (10 ml) was stirred for 6 h at 100° C. After cooled to room temperature, the mixture was concentrated under reduced pressure to remove the solvent. To the residue was added water, and the mixture was extracted with ethyl acetate. The extract was dried over anhydrous magnesium sulfate and evaporated. The residue was purified by silica gel column chromatography (n-hexane:ethyl acetate=9:1) to give the title compound (680 mg) having the following physical data.

MS(m/z): 425 (M+).

Reference example 27

2-(5-Diphenylmethylisoxazol-3-yl)methyl-5-methoxy-1,2,3,4-tetrahydronaphthalene

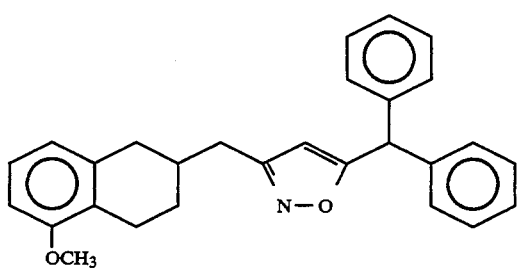

To a mixture of the compound prepared in reference example 26 (650 mg) and trifluoroacetic acid (6 ml) was added a solution of triethylsilane (350 mg) in methylene chloride (2 ml) at 0° C. The mixture was stirred for 1 h at room temperature. The mixture was concentrated under reduced pressure to remove the solvent. To the residue was added a saturated aqueous solution of sodium bicarbonate, and extracted with ethyl acetate. The extract was washed with water and a saturated aqueous solution of sodium chloride, successively, dried over anhydrous magnesium sulfate, and evaporated. The residue was purified by silica gel column chromatography (n-hexane:ethyl acetate=9:1) to give the title compound (525 mg) having the following physical data.

MS(m/z): 409 (M+).

Reference example 28

2-(5-Diphenylmethylisoxazol-3-yl)methyl-5-hydroxy-1,2,3,4-tetrahydronaphthalene

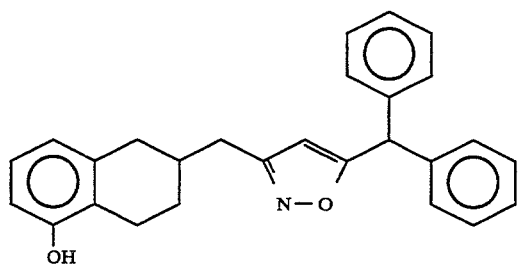

To a solution of the compound prepared in reference example 27 (470 mg) in methylene chloride (6 ml) was added boron tribromide (0.34 ml) at 0° C. The mixture was stirred for 2 h at the same temperature. The mixture was poured into ice water, and the mixture was extracted with ethyl acetate. The extract was washed with water and a saturated aqueous solution of sodium chloride, successively, dried over anhydrous magnesium sulfate, and evaporated. The residue was purified by silica gel column chromatography (n-hexane:ethyl acetate=5:1) to give the title compound (328 mg) having the following physical data.

MS(m/z): 395 (M+).

Reference example 29

2-(3,3-Dibromo-2-propenyl)-5-methoxy-1,2,3,4-tetrahydronaphthalene

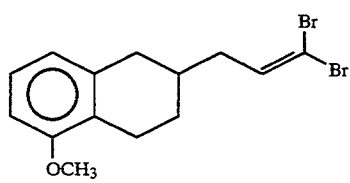

To a solution of carbon tetrabromide (19.5 g) in methylene chloride (50 ml) was added triphenylphosphine (30.8 g) at 0° C., and the mixture was stirred for 10 min. To the mixture was added a solution of 2-formylmethyl-5-methoxy1,2,3,4-tetrahydronaphthalene (4.09 g; the compound prepared by method described in the specification of the Japanese Patent Application No. 3-130467) in methylene chloride (25 ml) at 0° C. The mixture was stirred for 30 min at 0° C. To the mixture was gradually added n-hexane, and filtrated to remove triphenylphosphineoxide. The filtrate was washed with water and a saturated aqueous solution of sodium chloride, successively, dried over anhydrous magnesium sulfate, and evaporated. The residue was purified by silica gel column chromatography (n-hexane:ethyl acetate=24:1) to give the title compound (6.42 g) having the following physical data.

MS(m/z): 362, 360, 358 (M+).

Reference example 30

2-(2-Propynyl)-5-methoxy-1,2,3,4-tetrahydronaphthalene

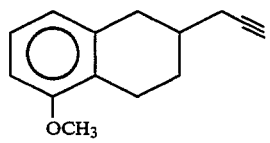

To a solution of the compound prepared in reference example 29 (6.20 g) in THF (70 ml) was added dropwise n-butyllithium (23.7 ml; 1.6M/L in hexane solution) at −70° C. The mixture was stirred for 30 min at −70° C. After quenched by addition of water and aqueous solution of ammonium chloride at the same temperature, the mixture was warmed up to room temperature. The mixture was extracted with hexane-ethyl acetate (6:1). The extract was washed with water and a saturated aqueous solution of sodium chloride, successively, dried over anhydrous magnesium sulfate, and evaporated. The residue was purified by silica gel column chromatography (n-hexane:ethyl acetate=24:1) to give the title compound (3.40 g) having the following physical data.

MS(m/z): 200 (M+).

Reference example 31

2-(5,5-Diphenyl-4-oxo-2-pentynyl)-5-methoxy-1,2,3,4-tetrahydronaphthalene

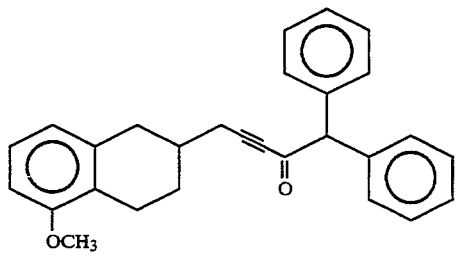

To a mixture of ethylmagnesium bromide (5.7 ml; 3.0M/L in ether solution) and THF (40 ml) was added dropwise a solution of the compound prepared in reference example 30 (3.0 g) in THF (20 ml) over a 10 min period. The mixture was stirred for 2 h at room temperature. To the mixture was added a solution of diphenylacetaldehyde (2.94 g) in THF (10 ml). The mixture was stirred for 2 h. After quenched by addition of ammonium chloride, the mixture was extracted with ether. The extract was washed with water and a saturated aqueous solution of sodium chloride, successively, dried over anhydrous magnesium sulfate, and evaporated. To a solution of the residue in ether (50 ml) was added manganese (IV) oxide (2.7 g) at room temperature. The mixture was stirred for 2 h. The mixture was filtrated, and evaporated. The residue was purified by silica gel column chromatography (n-hexane:ethyl acetate=7:1) to give the title compound (2.41 g) having the following physical data.

MS(m/z): 394 (M+).

Reference example 32

2-(3-Diphenylmethylisoxazol-5-yl)methyl-5-hydroxy-1,2,3,4-tetrahydronaphthalene

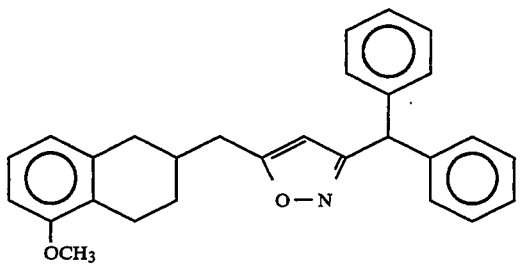

By the same procedure as a series of reactions of reference example 26→reference example 28, using the compound prepared in reference example 31, the title compound having the following physical data was given.

MS(m/z): 395 (M+).

Reference example 33

2-(4-Imino-2-hydroxy-5,5-diphenyl-2-pentenyl)-5-methoxy-1,2,3,4-tetrahydronaphthalene

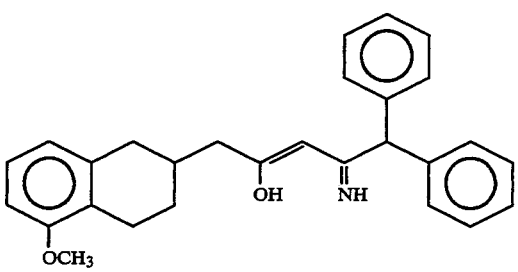

A mixture of the compound (600 mg) prepared by the same procedure as reference example 26, using the compound prepared in reference example 31, Raney nickel (300 mg; registered trade mark) and ethanol (5 ml) was stirred overnight under an atmosphere of hydrogen. The mixture was filtered through Celite (registered trade mark), and evaporated. The residue was purified by silica gel column chromatography (ethyl acetate:benzene=7:93) to give the title compound (325 mg) having the following physical data.

MS(m/z): 411 (M+).

Reference example 34

2-(3-Diphenylmethylisothiazol-5-yl)methyl-5-methoxy-1,2,3,4-tetrahydronaphthalene

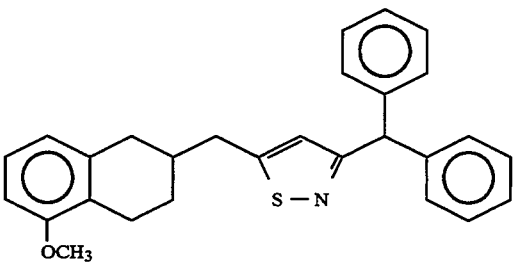

A mixture of the compound prepared in reference example 33 (255 mg), p-chloranil (153 mg), phosphorus pentasulfide (413 mg) and toluene (4 ml) was refluxed for 30 min. After cooled to room temperature, to the mixture was added benzene. The mixture was filtrated, and evaporated. The residue was purified by silica gel column chromatography (n-hexane:ethyl acetate=7:1) to give the title compound (128 mg) having the following physical data.

MS(m/z): 425 (M+).

Reference example 35

2-(3-Diphenylmethylisothiazol-5-yl)methyl-5-hydroxy-1,2,3,4-tetrahydronaphthalene

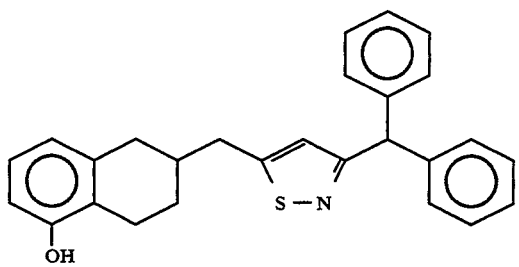

By the same procedure as reference example 7, using the compound prepared in reference example 34, the title compound (90 mg) having the following physical data was given.

MS(m/z): 411 (M+).

Example 1

Methyl [2-(4-diphenylmethylpyrazol-1-yl)methyl-1,2,3,4-tetrahydronaphthalen-5-yloxy]acetate

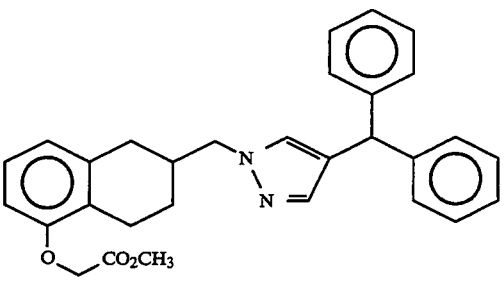

To a suspension of sodium hydride (60% containing, 68 mg) in DMF (2.0 ml) was added a solution of the compound prepared in reference example 4 (190 mg) in DMF (2.0 ml) with stirring at room temperature. After stirred for 30 min at room temperature, to the mixture was added a solution of the compound prepared in reference example 1 (280 mg) in DMF (2.0 ml). After stirred for 30 min, the mixture was quenched by addition of 1N hydrochloric acid. The mixture was extracted with ethyl acetate-n-hexane (1:2). The extract was washed with a saturated aqueous solution of sodium chloride, dried over anhydrous magnesium sulfate, and evaporated. The residue was purified by silica gel column chromatography (n-hexane:ethyl acetate=5:2) to give the title compound (90 mg) having the following physical data.

TLC: Rf 0.36 (n-hexane:ethyl acetate:=2:1); IR (cm$^{-1}$): $\nu$3061, 3027, 2928, 1762, 1741, 1602, 1586, 1494, 1466, 1374, 1346, 1207, 1120, 1031, 1018, 992, 918, 849, 764, 702.

Example 2

[2-(4-Diphenylmethylpyrazol-1-yl)methyl-1,2,3,4-tetrahydronaphthalen-5-yloxy]acetic acid

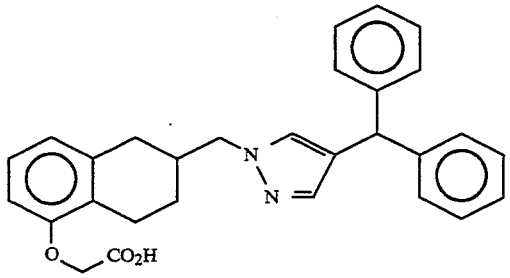

The compound prepared in example 1 (78 mg) was dissolved into THF (2.0 ml) and methanol (2.0 ml). 1N aqueous solution of sodium hydroxide (0.5 ml) was added to the solution with stirring at room temperature. This solution was stirred for 1 h at room temperature. After neutralized by addition of 2N hydrochloric acid (0.25 ml), the mixture was extracted with ethyl acetate. The extract was washed with a saturated aqueous solution of sodium chloride, dried over anhydrous magnesium sulfate, and evaporated. The residue was recrystallized from n-hexane-ethyl acetate to give the title compound (62 mg) having the following physical data.

TLC: Rf 0.31 (chloroform:methanol=17:3); NMR: $\delta$7.37–7.14 (1H, m), 7.02 (1H, t, J=8.0 Hz), 6.98 (1H, s), 6.67 (1H, d, J=8.0 Hz), 6.56 (1H, d, J=8.0 Hz), 5.35 (1H, s), 4.62 (2H, s), 4.50 (1H, brs), 4.15–3.93 (2H, m), 3.05–2.85 (1H, m), 2.71–2.10 (4H, m), 1.93–1.75 (1H, m), 1.45–1.20 (1H, m).

Example 2(a)~2(I)

By the same procedure as example 2, the compounds shown in the following table 3 were given by using the compound obtained from the same procedure as example 1 (provided that the compounds shown as (a) in the following table 3 were used instead of the compound prepared in reference example 4).

TABLE 3

| EX. No. | Structure of the compound (a) | Structure of the example compound | TLC | IR (cm$^{-1}$) |
|---|---|---|---|---|
| 2(a) | | | Rf 0.09 (chloroform:methanol = 9:1) | ν 2914, 2487, 1736, 1585, 1507, 1467, 1434, 1229, 1117, 767, 695. |
| 2(b) | | | Rf 0.21 (chloroform:methanol = 9:1) | ν 2918, 1741, 1598, 1585, 1498, 1464, 1378, 1281, 1210, 1121, 765, 695. |
| 2(c) | | | Rf 0.09 (chloroform:methanol = 9:1) | ν 3060, 2921, 1733, 1585, 1511, 1466, 1237, 1111, 1078, 705, 696. |

TABLE 3-continued

| EX. No. | Structure of the compound (a) | Structure of the example compound | TLC | |
|---|---|---|---|---|
| 2(d) | (structure) | (structure) | Rf 0.18 (chloroform:methanol = 9:1) | ν 2926, 1751, 1599, 1583, 1548, 1504, 1462, 1435, 1364, 1209, 763, 707. |
| 2(e) | (structure) | (structure) | Rf 0.18 (chloroform:methanol = 9:1) | ν 2931, 1764, 1666, 1585, 1498, 1466, 1440, 1402, 1271, 1202, 1125, 761, 712, 676. |
| 2(f) | (structure) | (structure) | Rf 0.18 (chloroform:methanol = 9:1) | ν 2924, 1739, 1688, 1506, 1489, 1468, 1409, 1210, 1123, 1048, 749, 700. |

TABLE 3-continued

| EX. No. | Structure of the compound (a) | Structure of the example compound | TLC | |
|---|---|---|---|---|
| 2(g) | [structure] | [structure] | Rf 0.28 (chloroform:methanol: acetic acid = 17:2:1) | ν 3449, 3060, 3028, 2479, 1732, 1586, 1495, 1466, 1454, 1309, 1220, 1156, 1109, 1083, 1032, 832, 758, 703, 637. |
| 2(h) | [structure] | [structure] | Rf 0.29 (chloroform:methanol = 3:1) | (film method) ν 3060, 3026, 2928, 1762, 1741, 1602, 1585, 1515, 1494, 1466, 1451, 1414, 1376, 1345, 1207, 1120, 1052, 1032, 1003, 962, 847, 761, 702. |
| 2(i) | [structure] | [structure] | Rf 0.25 (methylene chloride: methanol = 8:2) | NMR δ 8.43(2H, m), 7.70(1H, m), 7.50–7.10(8H, m), 6.98 (1H, t, J=8Hz), 6.70–6.50(2H, m), 5.53(1H, s), 4.57(2H, s), 4.08(2H, d, J=7Hz), 2.95(1H, m), 2.80–2.10(4H, m), 1.86 (1H, m), 1.38(1H, m). |

TABLE 3-continued

| EX. No. | Structure of the compound (a) | Structure of the example compound | TLC |
|---|---|---|---|
| 2(j) | (structure) | (structure) | Rf 0.22 (chloroform:methanol = 8:2) δ 7.40–7.00(12H, m), 6.80(1H, brs), 6.78(1H, d, J=8Hz), 6.60(1H, d, J=8Hz), 5.59(1H, m), 4.63(2H, s), 4.38(2H, m), 3.08–2.92(1H, m), 2.75–2.13(4H, m), 1.95–1.77(1H, m), 1.42–1.21(1H, m). |
| 2(k) | (structure) | (structure) | Rf 0.18 (chloroform:methanol = 8:2) δ 7.39–7.01(12H, m), 6.85(1H, brs), 6.76(1H, d, J=8Hz), 6.58(1H, d, J=8Hz), 5.64(1H, s), 4.56(2H, s), 4.24(2H, m), 3.05–2.85(1H, m), 2.73–2.12(4H, m), 1.94–1.76(1H, m), 1.41–1.12(1H, m). |
| 2(l) | (structure) | (structure) | Rf 0.16 (chloroform:methanol = 8:2) δ 7.41–6.99(13H, m), 6.78(1H, d, J=8Hz), 6.63(1H, d, J=8Hz), 5.26(1H, s), 4.62(2H, s), 4.03(2H, m), 3.03–2.84(1H, m), 2.73–2.13(4H, m), 1.95–1.76(1H, m), 1.43–1.20(1H, m). |

The example compounds shown in the table 3 are named as follows:

2(a) [2-(4,5-Diphenylimidazol-1-yl)methyl-1,2,3,4-tetrahydronaphthalen-5-yloxy]acetic acid 2(b) [2-(1,4,5-Triphenylimidazol-2-ylthio)methyl-1,2,3,4-tetrahydronaphthalen-5-yloxy]acetic acid 2(c) [2-(4,5-Diphenylimidazol-2-ylthio)methyl-1,2,3,4-tetrahydronaphthalen-5-yloxy]acetic acid 2(d) [2-(1,4,5-Triphenylimidazol-2-yloxy)methyl-1,2,3,4-tetrahydronaphthalen-5-yloxy]acetic acid 2(e) [2-(3,4,5-Triphenyl-2-oxo-2,3-dihydroimidazol-1-yl)methyl-1,2,3,4-tetrahydronaphthalen-5-yloxy]acetic acid 2(f) [2-(3-Phenyl-2-oxo-2,3-dihydrobenzimidazol-1-yl)methyl-1,2,3,4-tetrahydronaphthalen-5-yloxy]acetic acid 2(g) [2-(4-Diphenylmethylimidazol-1-yl)methyl-1,2,3,4-tetrahydronaphthalen-5-yloxy]acetic acid 2(h) [2-(3-Diphenylmethylpyrazol-1-yl)methyl-1,2,3,4-tetrahydronaphthalen-5-yloxy]acetic acid 2(i) [2-(4-((3-Pyridyl)phenylmethyl)pyrazol-1-yl)methyl-1,2,3,4-tetrahydronaphthalen-5-yloxy]acetic acid 2(j) [2-(4-Diphenylmethyl-1,2,3-triazol-2-yl)methyl-1,2,3,4-tetrahydronaphthalen-5-yloxy]acetic acid 2(k) [2-(4-Diphenylmethyl-1,2,3-triazol-1-yl)methyl-1,2,3,4-tetrahydronaphthalen-5-yloxy]acetic acid 2(l) [2-(4-Diphenylmethyl-1,2,3-triazol-3-yl)methyl-1,2,3,4-tetrahydronaphthalen-5-yloxy]acetic acid Example 3

Methyl [2-[2-(4,5-diphenylimidazol-1-yl)ethyl]-1,2,3,4-tetrahydronaphthalen-5-yloxy]acetate

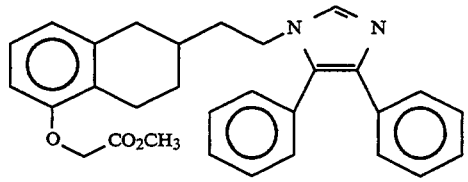

By the same procedure as example 1 (provided that 4,5-diphenylimidazole was used instead of the compound prepared in reference example 4), the title compound having the following physical data was given by using the compound obtained from the same procedure as reference example 1, using methyl [2-(2-hydroxyethyl)-1,2,3,4-tetrahydronaphthalen-5-yloxy]acetate instead of methyl (2-hydroxymethyl-1,2,3,4-tetrahydronaphthalen-5-yloxy) acetate.

NMR: δ7.64 (1H, s), 7.60–7.10 (10H, m), 7.02 (1H, t, J=7 Hz), 6.62 (1H, d, J=7 Hz), 6.48 (1H, d, J=7 Hz), 4.62 (2H, s), 3.92 (2H, t, J=6 Hz), 3.78 (3H, s), 3.00–2.10 (5H, m), 1.95–1.50 (3H, m), 1.25 (1H, m); IR (cm$^{-1}$): ν3434, 2925, 1761, 1603, 1585, 1507, 1466, 1441, 1373, 1245, 1207, 1118, 1022, 954, 918, 773, 721, 700, 654.

Example 4

[2-[2-(4,5-Diphenylimidazol-1-yl)ethyl]-1,2,3,4-tetrahydronaphthalen-5-yloxy]acetic acid

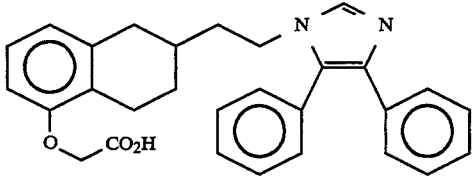

By the same procedure as example 2, by using the compound prepared in example 3, the title compound having the following physical data was given.

mp.: 197° C.; TLC: Rf 0.16 (methylene chloride:methanol=9:1); IR (cm$^{-1}$): ν3453, 2922, 1734, 1585, 1551, 1467, 1441, 1244, 1113, 767, 697.

Example 4(a)~4(f)

By the same procedure as example 2, the compounds shown in the following table 4 were given by using the compound obtained from the same procedure as example 3, using the compound shown as (a) in the following table 4 instead of 4,5-diphenylimidazole.

TABLE 4

| EX. No. | Structure of the compound (a) | Structure of the example compound | TLC | IR (cm$^{-1}$) |
|---|---|---|---|---|
| 4(a) | | | Rf 0.22 (methylene chloride: methanol = 9:1) | ν 3449, 2918, 1732, 1582, 1495, 1465, 1423, 1200, 1117, 764, 702, 693. |

TABLE 4-continued

| EX. No. | Structure of the compound (a) | Structure of the example compound | TLC | IR (cm$^{-1}$) |
|---|---|---|---|---|
| 4(b) | | | Rf 0.16 (methylene chloride: methanol = 9:1) | $\nu$ 2923, 1897, 1735, 1585, 1466, 1236, 1111, 765, 695. |
| 4(c) | | | Rf 0.32 (methylene chloride: methanol = 9:1) | $\nu$ 2925, 1736, 1583, 1544, 1501, 1465, 1390, 1335, 1203, 1118, 764, 705. |
| 4(d) | | | Rf 0.32 (methylene chloride: methanol = 9:1) | $\nu$ 2928, 1724, 1696, 1653, 1585, 1500, 1455, 1406, 1382, 1230, 1113, 756, 696. |
| 4(e) | | | Rf 0.32 (methylene chloride: methanol = 9:1) | $\nu$ 2911, 1753, 1675, 1587, 1506, 1489, 1415, 1268, 1213, 1126, 761, 744, 730, 695. |
| 4(f) | | | Rf 0.32 (chloroform: methanol = 4:1) | $\nu$ 3027, 2914, 2531, 1746, 1601, 1584, 1495, 1466, 1431, 1350, 1313, 1265, 1218, 1121, 1014, 761, 728, 705, 678. |

The example compounds shown in the table 4 are named as follows:

4(a) [2-(2-(1,4,5-Triphenylimidazol-2-ylthio)ethyl)-1,2,3,4-tetrahydronaphthalen-5-yloxy]acetic acid 4(b) [2-(2-(4,5-Diphenylimidazol-2-ylthio)ethyl)-1,2,3,4-tetrahydronaphthalen-5-yloxy]acetic acid 4(c) [2-(2-(1,4,5-Triphenylimidazol-2-yloxy)ethyl)-1,2,3,4-tetrahydronaphthalen-5-yloxy]acetic acid 4(d) [2-(2-(3,4,5-Triphenyl-2-oxo-2,3-dihydroimidazol-1-yl)ethyl)-1,2,3,4-tetrahydronaphthalen-5-yloxy]acetic acid 4(e) [2-(2-(3-Phenyl-2-oxo-2,3-dihydrobenzimidazol-1-yl)ethyl)-1,2,3,4-tetrahydronaphthalen-5-yloxy]acetic acid 4(f) [2-(2-(4-Diphenylmethylpyrazol-1-yl)ethyl)-1,2,3,4-tetrahydronaphthalen-5-yloxy]acetic acid

Example 5

Methyl [1-[2-(4,5-diphenylimidazol-1-yl)ethyl]-1,2,3,4-tetrahydronaphthalen-5-yloxy]acetate

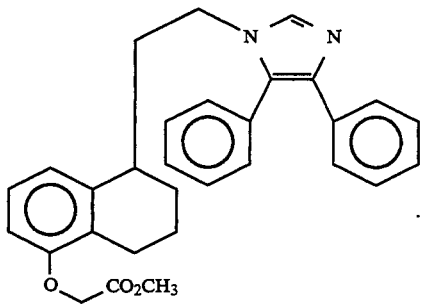

By the same procedure as example 3, by using methyl [1-(2-hydroxyethyl)-1,2,3,4-tetrahydronaphthalen-5-yloxy]acetate instead of methyl [2-(2-hydroxyethyl)-1,2,3,4-tetrahydronaphthalen-5-yloxy]acetate, the title compound having the following physical data was given.

IR (cm$^{-1}$): ν3066, 2932, 2861, 2361, 1761, 1676, 1603, 1581, 1506, 1463, 1442, 1371, 1339, 1244, 1210, 1121, 1073, 1022, 954, 918, 849, 775, 755, 721, 699; MS(m/z): 466 (M+).

Example 6

[1-[2-(4,5-Diphenylimidazol-1-yl)ethyl]-1,2,3,4-tetrahydronaphthalen-5yloxy]acetic acid

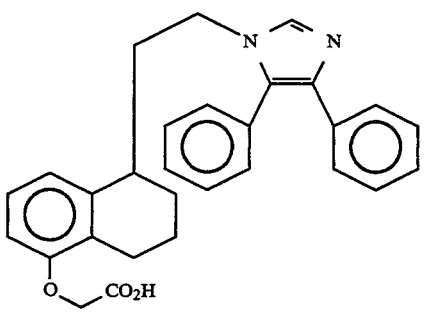

By the same procedure as example 2, by using the compound prepared in example 5, the title compound having the following physical data was given.

TLC: Rf 0.17 (methylene chloride:methanol = 10:1); IR (cm$^{-1}$): ν3449, 3058, 2932, 2862, 1736, 1603, 1581, 1508, 1463, 1444, 1339, 1230, 1115, 1075, 920, 885, 775, 722, 700.

Example 6(a)~6(d)

By the same procedure as example 2, the compounds shown in the following table 5 were given by using the compound obtained from the same procedure as example 3, and that shown as (a) in the following table 5 instead of 4,5-diphenylimidazole.

TABLE 5

| EX. No. | Structure of the compound (a) | Structure of the example compound | TLC | IR (cm$^{-1}$) |
|---|---|---|---|---|
| 6(a) | | | Rf 0.11 (methylene chloride: methanol = 10:1) | ν 3061, 2928, 2859, 1898, 1736, 1582, 1510, 1491, 1464, 1407, 1373, 1340, 1306, 1234, 1180, 1111, 1073, 1046, 1027, 917, 883, 766, 696, 588, 537. |
| 6(b) | | | Rf 0.18 (methylene chloride: methanol = 10:1) | ν 3059, 2931, 2863, 1737, 1695, 1656, 1597, 1583, 1499, 1450, 1402, 1373, 1313, 1224, 1176, 1117, 1074, 1027, 919, 886, 802, 760, 712, 699, 657, 515. |

| EX. No. | Structure of the compound (a) | Structure of the example compound | TLC | IR (cm$^{-1}$) |
|---|---|---|---|---|
| 6(c) | | | Rf 0.29 (chloroform: methanol = 4:1) | ν 3027, 2932, 1736, 1582, 1494, 1464, 1373, 1217, 1118, 1079, 1015, 875, 776, 752, 702. |
| 6(d) | | | Rf 0.28 (chloroform: methanol = 4:1) | ν 2932, 1735, 1464, 1222, 1116, 703. |

The example compounds shown in the table 5 are named as follows:

6(a) [1-(2-(4,5-Diphenylimidazol-2-ylthio)ethyl)-1,2,3,4-tetrahydronaphthalen-5-yloxy]acetic acid 6(b) [1-(2-(1,4,5-Triphenyl-2-oxo-2,3-dihydroimidazol-3-yl)ethyl)-1,2,3,4-tetrahydronaphthalen-5-yloxy]acetic acid 6(c) [1-(2-(4-Diphenylmethylpyrazol-1-yl)ethyl)-1,2,3,4-tetrahydronaphthalen-5-yloxy]acetic acid 6(d) [1-(2-(4-((3-Pyridyl)phenylmethyl)pyrazol-1-yl)ethyl)-1,2,3,4-tetrahydronaphthalen-5-yloxy]acetic acid Example 7

Methyl [1-[2-(3-diphenylmethyl-1,2,4-oxadiazol-5-yl)ethyl]-1,2,3,4-tetrahydronaphthalen-5-yloxy]acetate

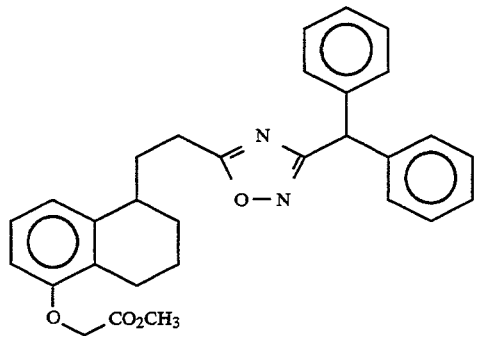

A suspension of the compound prepared in reference example 6 (400 mg) in toluene (20 ml) was stirred overnight. The mixture was concentrated under reduced pressure. The residue was purified by silica gel column chromatography (n-hexane:ethyl acetate=4:1) to give the title compound (305 mg) having the following physical data.

MS(m/z): 482 (M+), 423, 315, 273, 263, 250, 167; IR (cm$^{-1}$): ν3029, 2935, 1762, 1739, 1581, 1496, 1464, 1374, 1210, 1121 1080, 1033, 846, 777, 702.

Example 8

[1-[2-(3-Diphenylmethyl-1,2,4-oxadiazol-5-yl)ethyl]-1,2,3,4-tetrahydronaphthalen-5-yloxy]acetic acid

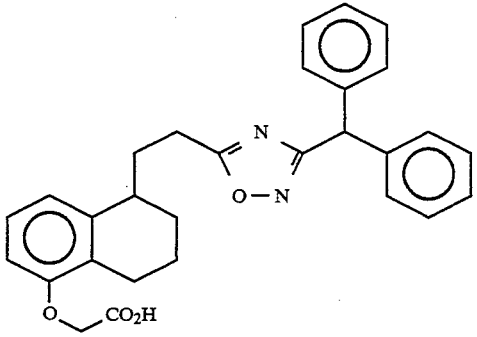

By the same procedure as example 2, by using the compound prepared in example 7, the title compound having the following physical data was given.

TLC: Rf 0.11 (methanol:methylene chloride=1:9); IR (cm$^{-1}$): ν2935, 1748, 1708, 1578, 1496, 1465, 1429, 1377, 1240, 1123, 1032, 923, 782, 747, 722, 702, 634, 587.

Example 8(a) and (b)

By the same procedure as a series of reaction of example 7→example 8, the compounds shown in the following table 6 were given by using methyl [2-((1-amino-2,2-diphenylethylidene)aminoxycarbonylmethyl)-1,2,3,4-tetrahydronaphthalen-5-yloxy]acetate or the compound prepared in reference example 23 instead of the compound prepared in reference example 6.

room temperature, the mixture was filtrated, and evaporated. The residue was purified by silica gel column chromatography (ethyl acetate:n-hexane=1:4) to give the title compound (145 mg) having the following physical data.

TLC: Rf 0.28 (ethyl acetate:n-hexane=1:3); IR (cm$^{-1}$): ν3027, 2926, 1762, 1585, 1495, 1466, 1452, 1437, 1345, 1282, 1207, 1156, 1120, 1099, 1032, 997, 839, 767, 750, 702.

TABLE 6

| EX. No. | Structure of the example compound | NMR |
|---|---|---|
| 8(a) | (structure) | δ 7.40-7.20(10H, m), 7.06(1H, t, J=8Hz), 6.72(1H, d, J=8Hz), 6.53(1H, d, J=8Hz), 5.60(1H, s), 4.65(2H, s), 3.10-1.80(8H, m), 1.50(1H, m). |
| 8(b) | (structure) | δ 7.40-7.10(10H, m), 7.05(1H, t, J=8Hz), 6.85(1H, d, J=8Hz), 6.53(1H, d, J=8Hz), 5.72(1H, s), 4.62(2H, s), 2.90-1.60(11H, m). |

The example compounds shown in the table 6 are named as follows:

8(a) [2-(3-Diphenylmethyl-1,2,4-oxadiazol-5-yl)methyl-1,2,3,4-tetrahydronaphthalen-5-yloxy]acetic acid 8(b) [1-(2-(5-Diphenylmethy-1,2,4-oxadiazol-3-yl)ethyl)-1,2,3,4-tetrahydronaphthalen-5-yloxy]acetic acid

Example 9

Methyl [2-(4-diphenylmethyloxazol-2-yl)methyl-1,2,3,4-tetrahydronaphthalen-5-yloxy]acetate

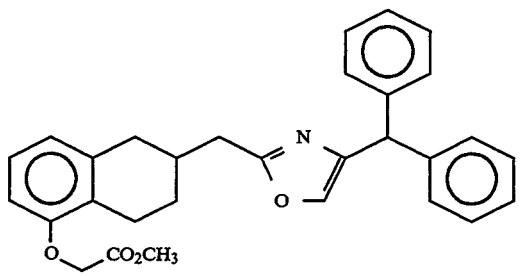

To a suspension of the compound prepared in reference example 12 (132 mg) and potassium carbonate (93 mg) in acetone (2.0 ml) was stirring added methyl bromoacetate (0.063 ml) with stirring at room temperature. The mixture was stirred for 4 h at 40° C. After cooled to

Example 10

[2-(4-Diphenylmethyloxazol-2-yl)methyl-1,2,3,4-tetrahydronaphthalen-5-yloxy]acetic acid

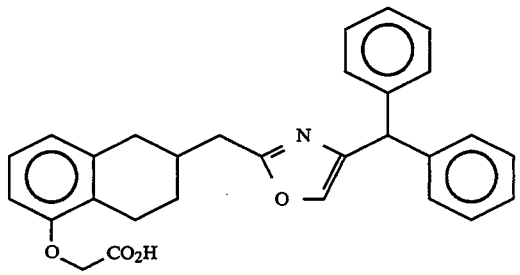

By the same procedure as example 2, by using the compound prepared in example 9, the title compound having the following physical data was given.

mp.: 129.5°~131.5° C.; TLC: Rf 0.24 (methanol:chloroform=3:17); IR (cm$^{-1}$): ν3029, 2923, 1748, 1585, 1570, 1495, 1467, 1453, 1433, 1307, 1243, 1212, 1120, 1032, 984, 913, 764, 730, 700.

Example 11

Methyl [2-(2-Diphenylmethyloxazol-4-yl)methyl-1,2,3,4-tetrahydronaphthalen-5-yloxy]acetate

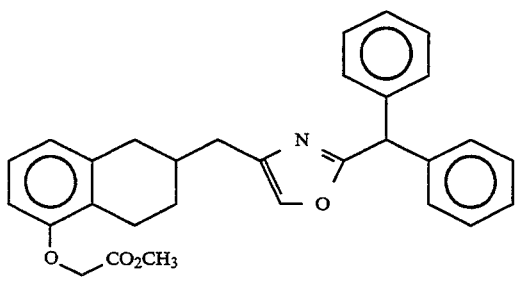

By the same procedure as example 9, by using the compound prepared in example 16, the title compound having the following physical data was given.

mp.: 91°~93° C.; TLC: Rf 0.32 (n-hexane:ethyl acetate=3:1); IR (cm$^{-1}$): $\nu$3100, 3028, 2933, 1756, 1601, 1585, 1566, 1495, 1463, 1378, 1345, 1275, 1202, 1168, 1117, 1086, 1031, 987, 955, 770, 757, 742, 718, 701, 538.

Example 12

[2-(2-Diphenylmethyloxazol-4-yl)methyl-1,2,3,4-tetrahydronaphthalen-5-yloxy]acetic acid

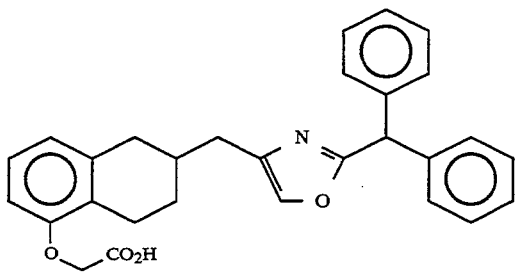

By the same procedure as example 2, by using the compound prepared in example 11, the title compound having the following physical data was given.

mp.: 158°~159.5° C.; TLC: Rf 0.19 (chloroform:methanol=9:1); IR (cm$^{-1}$): $\nu$3414, 3062, 2925, 1756, 1603, 1585, 1557, 1495, 1467, 1451, 1435, 1345, 1118, 968, 765, 736, 720, 698, 648, 585.

Example 12(a)

[2-(2-((3-Pyridyl)phenylmethyl)oxazol-4-yl)methyl-1,2,3,4-tetrahydronaphthalen-5-yloxy]acetic acid

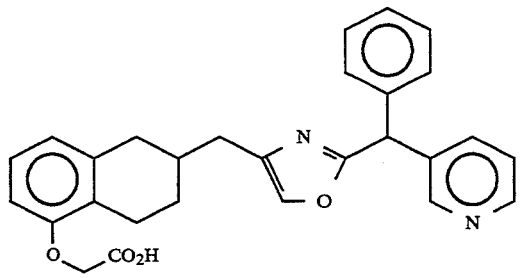

By the same procedure as a series of reaction of reference example 16→example 11→example 12, the title compound having the following physical data was given by using the compound obtained by the same procedure as reference example 15 (provided that sodium (3-pyridyl)phenylacetate was used instead of sodium diphenylacetic acid).

NMR: δ8.52-8.30 (2H, m), 7.78-7.64 (1H, m), 7.41-7.15 (7H, m), 7.00 (1H, t, J=8 Hz), 6.68 (1H, d, J=8 Hz), 6.57 (1H, d, J=8 Hz), 5.72 (1H, s), 4.61 (2H, s), 3.04-1.90 (8H, m), 1.53-1.33 (1H, m).

Example 13

Methyl [2-(2-diphenylmethyl-5-ethyloxazol-4-yl)methyl-1,2,3,4-tetrahydronaphthalen-5-yloxy]acetate

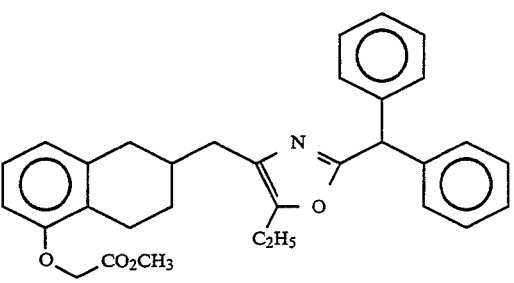

To diphenylacetyl chloride (6 mmol) was added the compound prepared in reference example 17 under cooling with ice bath. The mixture was stirred overnight at 100° C. After cooled to room temperature, the mixture was poured into water. The mixture was extracted with ethyl acetate. The extract was washed with water and a saturated aqueous solution of sodium chloride, successively, dried over anhydrous magnesium sulfate, and evaporated. The residue was purified by silica gel column chromatography (first time: n-hexane:ethyl acetate=5:1, second time: benzene:ethyl acetate=97:3) to give the title compound (93 mg) having the following physical data.

TLC: Rf 0.29 (benzene:ethyl acetate=19:1); IR (cm$^{-1}$): $\nu$3063, 3029, 2926, 1763, 1603, 1583, 1566, 1455, 1437, 1377, 1283, 1206, 1121, 1032, 854, 767, 748, 702.

Example 14

[2-(2-Diphenylmethyl-5-ethyloxazol-4-yl)methyl-1,2,3,4-tetrahydronaphthalen-5-yloxy]acetic acid

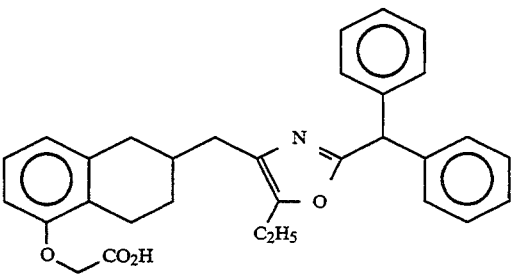

By the same procedure as example 2, by using the compound prepared in example 13, the title compound having the following physical data was given.

mp.: 150.5°~151.5° C.; TLC: Rf 0.27 (chloroform:methanol=9:1); IR (cm$^{-1}$): $\nu$3030, 2974, 2932, 2504, 1907, 1718, 1585, 1562, 1495, 1343, 1249, 1211, 1155, 1113, 1032, 767, 747, 727, 701, 633, 586.

Example 15

Methyl [2-(2-diphenylmethylimidazol-4-yl)methyl-1,2,3,4-tetrahydronaphthalen-5-yloxy]acetate

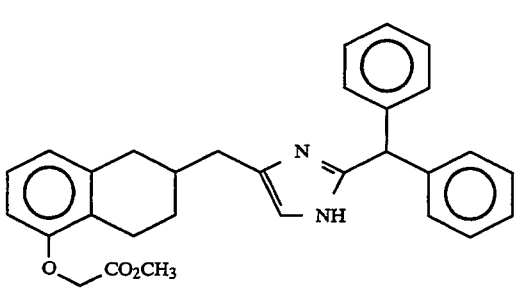

A mixture of the compound prepared in reference example 18 (350 mg) and the compound prepared in reference example 19 (450 mg) in chloroform was refluxed for 18 h. After cooled to room temperature, the mixture was quenched by addition of an aqueous solution of sodium bicarbonate. The mixture was extracted with ethyl acetate. The extract was washed with water and a saturated aqueous solution of sodium chloride, successively, dried over anhydrous magnesium sulfate, and evaporated. The residue was purified by silica gel column chromatography (n-hexane:ethyl acetate=1:1) to give the title compound (181 mg) having the following physical data.

TLC: Rf 0.23 (ethyl acetate:n-hexane=1:1); IR (cm$^{-1}$): $\nu$3026, 2925, 2362, 1762, 1585, 1495, 1466, 1455, 1438, 1208, 1120, 766, 701, 589.

Example 16

[2-(2-Diphenylmethylimidazol-4-yl)methyl-1,2,3,4-tetrahydronaphthalen-5-yloxy]acetic acid

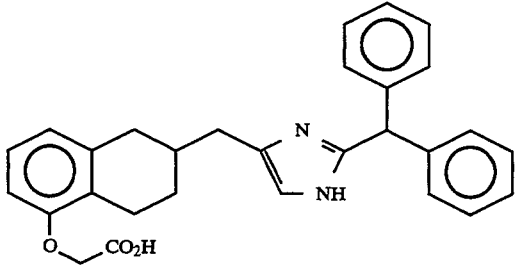

By the same procedure as example 2, the using the compound prepared in example 15, the title compound having the following physical data was given.

mp.: 170° C.; TLC: Rf 0.25 (chloroform:methanol:acetic acid=17:2:1); IR (cm$^{-1}$): $\nu$3424, 3030, 2922, 1955, 1641, 1586, 1496, 1411, 1329, 1237, 1106, 1081, 1005, 768, 700, 587.

Example 17

Octyl [2-(4-diphenylmethylpyrazol-1-yl)methyl-1,2,3,4-tetrahydronaphthalen-5-yloxy]acetate

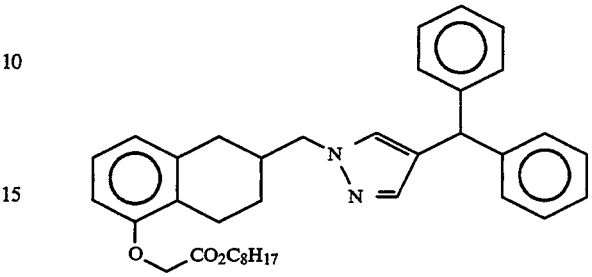

The compound prepared in example 2 (0.453 g) was dissolved into oxalyl chloride (3 ml). The mixture was stirred for 1 h at room temperature. The mixture was concentrated under reduced pressure to remove excess oxalyl chloride. The residue was dissolved into pyridine (2 ml), and to this solution was added n-octyl alcohol (156 mg). The mixture was stirred for 1 h at room temperature. The mixture was diluted with ethyl acetate. The mixture was washed with water, dried over anhydrous magnesium sulfate, and evaporated. The residue was purified by silica gel column chromatography (ethyl acetate:n-hexane=4:1) to give the title compound (0.48 g) having the following physical data.

MS(m/z): 565 (M$^+$+1); TLC: Rf 0.33 (n-hexane:ethyl acetate=3:1).

Example 18

[2-(4-Diphenylmethylpyrazol-1-yl)methyl-1,2,3,4-tetrahydronaphthalen-5-yloxy]acetamide

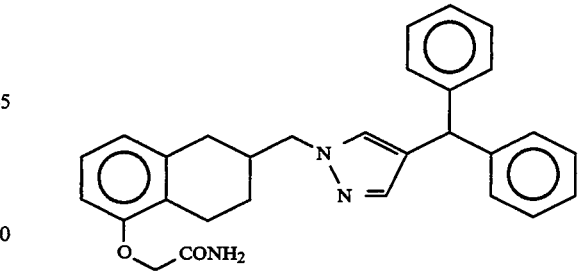

The compound prepared in example 2 (452 mg) was dissolved into oxalyl chloride (2 ml). The mixture was stirred for 1 h at room temperature. The mixture was concentrated under reduced pressure to remove excess oxalyl chloride. The residue was dissolved into methylene chloride (5.0 ml). After cooled to 0° C., the mixture was suspended by bubbling the gaseous ammonia into the mixture. After stirred for 30 min at room temperature, the precipitate was filtrated off, and the filtrate evaporated. The residue was purified by silica gel column chromatography (methanol:methylene chloride=1:4) to give the title compound (420 mg) having the following physical data. TLC: Rf 0.22 (methylene chloride: methanol=4:1);

MS(m/z): 451 (M$^+$).

Example 19

Amide of [2-(4-diphenylmethylpyrazol-1-yl)methyl-1,2,3,4-tetrahydronaphthalen-5-yloxy]acetic acid with glycine

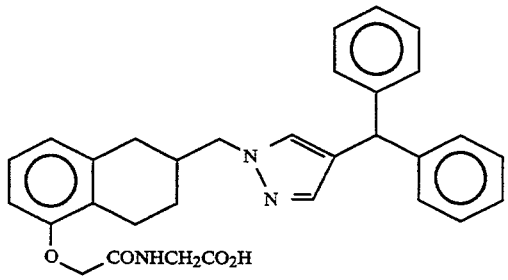

A mixture of the carboxylic acid prepared in example 2 (452 mg), glycine-tert-butyl ester hydrochloride (158 mg), 2-chloro-1-methylpyridinum iodide (307 mg) and triethylamine (0.42 ml) was dissolved into methylene chloride (5.0 ml). The mixture was stirred for 4 h at room temperature, and concentrated under reduced pressure. The residue was purified by silica gel column chromatography (ethyl acetate:n-hexane=1:1) to give the condensing compound. To a solution of the condensing compound in methylene chloride (3.0 ml) was added trifluoroacetic acid (3.0 ml). The mixture was stirred for 3 h at room temperature. The mixture was concentrated under reduced pressure. The residue-was purified by silica gel column chromatography (methanol:methylene chloride=1:9) to give the title compound (403 mg) having the following physical data.

TLC: Rf 0.21 (methylene chloride:methanol=9:1); MS(m/z): 509(M+).

Example 20

[1-[3-(4-Diphenylmethylpyrazol-1-yl)propyl]-1,2,3,4-tetrahydronaphthalen-5-yloxy]acetic acid

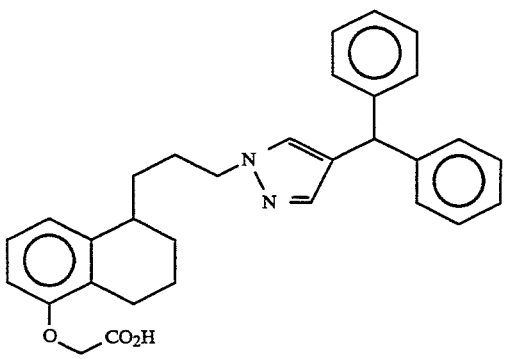

By the same procedure as a series of reactions of reference example 1→example 1→example 2, by using methyl [1-(3-hydroxypropyl)-1,2,3,4-tetrahydronaphthalen-5-yloxy]acetate instead of methyl (2-hydroxymethyl-1,2,3,4-tetrahydronaphthalen-5-yloxy)acetate, the title compound having the following physical data was given.

TLC: Rf 0.30 (chloroform:methanol=4:1); IR (cm$^{-1}$): ν3027, 2932, 2862, 1736, 1602, 1582, 1494, 1464, 1374, 1340, 1216, 1118, 1080, 1015, 874, 752, 702.

Example 21

[2-[3-(4-((3-Pyridyl)phenylmethyl)pyrazol-1-yl)-1-propenyl]-1,2,3,4-tetrahydronaphthalen-5-yloxy]acetic acid

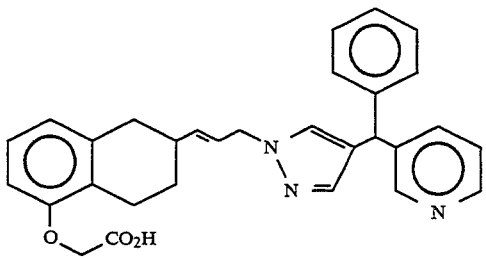

By the same procedure as a series of reactions of example 1→example 2, the title compound having the following physical data was given by using 4-((3-pyridyl)phenylmethyl)pyrazole instead of the compound prepared in reference example 4, and by using the compound obtained by the same procedure as reference 1, using methyl [2-(3-hydroxy-1-propenyl)-1,2,3,4-tetrahydronaphthalen-5-yloxy]acetate instead of methyl (2-hydroxymethyl-1,2,3,4-tetrahydronaphthalen-5-yloxy)acetate.

NMR: δ8.55 (1H, s), 8.43 (1H, d, J=4 Hz), 7.62 (1H, d, J=7 Hz), 7.37–7.00 (10H, m), 6.69 (1H, d, J=8 Hz), 6.62 (1H, d, J=8 Hz), 6.32–6.21 (2H, m), 5.40 (1H, s), 4.88 (2H, d, J=6 Hz), 4.59 (1H, s), 3.02–1.85 (6H, m), 1.56–1.40 (1H, m).

Example 22

[2-(4-(Diphenylmethyl)pyrazol-1-yl)methyl-3,4-dihydronaphthalen-5-yloxy]acetic acid

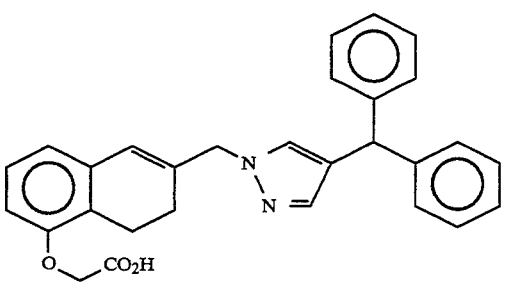

By the same procedure as a series of reactions of example 1→example 2, the title compound having the following physical data was given by using the compound in reference example 4 and the compound obtained from the same procedure as reference example 1, using methyl (2-hydroxymethyl-3,4-dihydronaphthalen-5-yloxy)acetate instead of methyl (1-hydroxymethyl-1,2,3,4-tetrahydronaphthalen-5-yloxy)acetate.

NMR: δ8.00 (1H, brs), 7.31–7.12 (11H, m), 7.06 (1H, s), 7.04 (1H, t, J=8 Hz), 6.66 (1H, d, J=8 Hz), 6.62 (1H, d, J=8 Hz), 6.18 (1H, s), 5.35 (1H, s), 4.78 (2H, s), 4.58 (2H, s), 2.84 (2H, t J=8 Hz), 2.13 (2H, d, J=8 Hz).

Example 22(a)

[2-(4-((3-Pyridyl)phenylmethyl)pyrazol-1-yl)methyl-3,4-dihydronaphthalen-5-yloxy]acetic acid

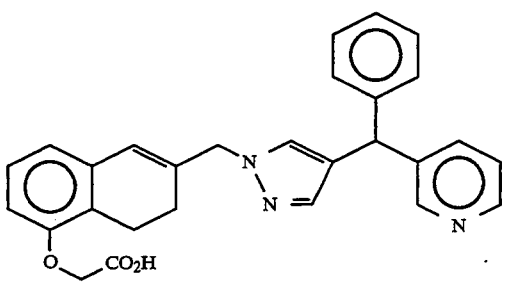

By the same procedure as example 22, by using 4-((3-pyridyl)phenylmethyl)pyrazole instead of the compound prepared in reference example 4, the title compound having the following physical data was given.

NMR: δ8.52 (2H, m), 7.60 (1H, m), 7.40–7.00 (10H, m), 6.69 (2H, d, J=8 Hz), 6.23 (1H, s), 5.40 (1H, s), 4.80 (2H, s), 4.60 (2H, s), 2.89 (2H, t, J=9 Hz), 2.14 (2H, t, J=9 Hz).

The title compound thus obtained was further separated by high performance liquid chromatography (ethanol:n-hexane=3:7; containing 0.5% acetic acid) to give each isomers having the following physical data. (+) isomer:HPLC:$t_R$=67.93 min (ethanol:n-hexane=3:7; containing 0.5% acetic acid); $[\alpha]_D$+10.7 (c0.7, chloroform). (−) isomer:HPLC:$t_R$=77.33 min (ethanol:n-hexane=3:7; containing 0.5% acetic acid); $[\alpha]_D$−9.8 (c0.8, chloroform).

Example 23

[1-(2-(4-((3-Pyridyl)phenylmethyl)pyrazol-1-yl)ethylidene)-1,2,3,4-tetrahydronaphthalen-5-yloxy]acetic acid

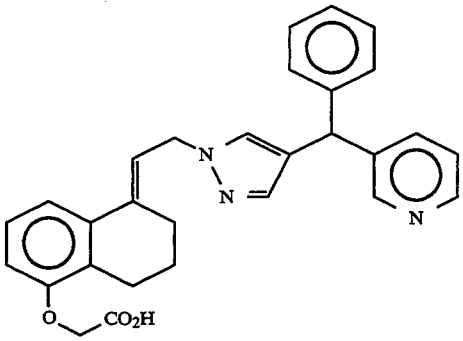

By the same procedure as a series of reactions of example 1→example 2, the title compound having the following physical data was given by using 4-((3-pyridyl)phenylmethyl)pyrazole instead of the compound prepared in reference example 4 and the compound obtained from the same procedure as reference example 1, using methyl (1-(2-hydroxyethylidene)-1,2,3,4-tetrahydronaphthalen-5-yloxy)acetate instead of methyl (2-hydroxymethyl-1,2,3,4-tetrahydronaphthalen-5-yloxy)acetate.

NMR: δ8.65–8.42 (2H, m), 7.73–7.65 (1H, d, J=7 Hz), 7.40–6.96 (11H, m), 6.62 (1H, d, J=8 Hz), 6.12 (1H, t, J=5 Hz), 5.43 (1H, s), 4.82 (2H, d, J=5 Hz), 4.61 (2H, s), 3.05 (2H, t, J=6 Hz), 2.43 (2H, t, J=6 Hz), 1.82–1.68 (2H, m).

Example 24

[2-(4-((1-Imidazolyl)phenylmethyl)pyrazol-1-yl)methyl-1,2,3,4-tetrahydronaphthalen-5-yloxy]acetic acid

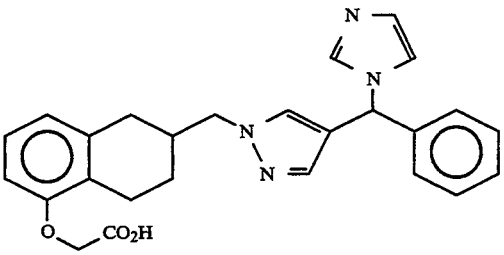

1) To a solution of the compound prepared in reference example 20 (480 mg) in THF-methanol (2:1, 4 ml) was added 1N aqueous solution of sodium hydroxide (2.0 ml) with stirring at room temperature. The mixture was stirred for 30 min at room temperature. After neutralized by addition of 1N hydrochloric acid (2.0 ml), the mixture was extracted with ethyl acetate. The extract was washed with a saturated aqueous solution of sodium chloride, dried over anhydrous magnesium sulfate, and evaporated.

2) To a solution of the residue in methanol (4 ml) was added sodium borohydride (100 mg) at 0° C. After stirred for 3 h at room temperature, the mixture was concentrated under reduced pressure. After the residue was acidified by addition of 1N hydrochloric acid, the mixture was extracted with ethyl acetate. The extract was washed with a saturated aqueous solution of sodium chloride, dried over anhydrous magnesium sulfate, and evaporated.

3) A solution of the residue in ethyl acetate-methanol (9:1, 3 ml) was cooled at 0° C. To the mixture was added excess amount of an ethereal solution of diazomethane. After standed for 10 min at room temperature, the mixture was concentrated under reduced pressure. The residue was purified by silica gel column chromatography (n-hexane:ethyl acetate=5:2).

4) A mixture of the obtained compound (280 mg), imidazole hydrobromide (700 mg), molecular sieves 4A (1 g) and DMF (3 ml) was stirred for 5 h at 110° C. After cooled to room temperature, the mixture was diluted with n-hexane-ethyl acetate (1:1). The organic layer was washed with water and a saturated aqueous solution of sodium chloride, successively, dried over anhydrous magnesium sulfate, and evaporated. The residue was purified by silica gel column chromatography (methanol:chloroform=1:99→2:98→3:97).

5) By the same procedure as example 2, using the obtained compound, the title compound having the following physical data was given.

NMR: δ8.10–7.60 (2H, m), 7.42–7.06 (8H, m), 6.99 (1H, t, J=8 Hz), 6.92 (1H, s), 6.70–6.50 (2H, m), 6.45 (1H, s), 4.57 (2H, s), 4.15–3.90 (2H, m), 3.05–2.85 (1H, m), 2.74–2.18 (4H, m), 1.93–1.74 (1H, m), 1.46–1.20 (1H, m).

Example 25

[2-(5-Diphenylmethylisoxazol-3-yl)methyl-1,2,3,4-tetrahydronaphthalen-5-yloxy]acetic acid

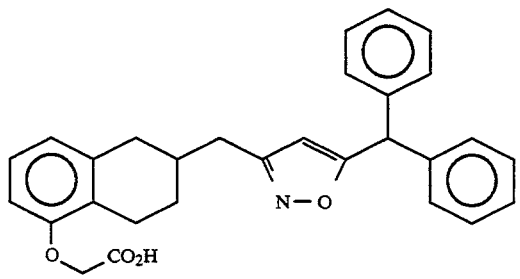

By the same procedure as a series of reactions of example 9→example 10, using the compound prepared in reference example 28, the title compound having the following physical data was given.

NMR: δ7.40–7.02 (11H, m), 7.00 (1H, t, J=8 Hz), 6.72 (1H, d, J=8 Hz), 6.60 (1H, d, J=8 Hz), 5.60 (1H, s), 5.43 (1H, s), 4.53 (2H, s), 3.06–2.85 (1H, m), 2.76–2.10 (4H, m), 1.95–1.75 (1H, m), 1.45–1.20 (1H, m).

Example 25(a) or (b)

By the same procedure as example 25, the compounds shown in the following table 7 were given by using compounds prepared in reference example 32 and reference example 35 instead of the compound prepared in reference example 28.

Example 26

[1-(2-(4-Diphenylmethylpyrazol-1-yl)ethyl)indan-4-yloxy]acetic acid

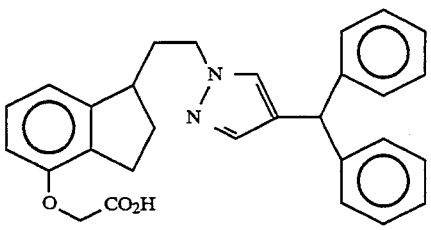

By the same procedure as a series of reactions of reference example 1→example 1→example 2, using methyl [1-(2-hydroxyethyl)-indan-4-yloxy]acetate instead of methyl (2-hydroxymethyl-1,2,3,4-tetrahydronaphthalen-5yloxy)acetate, the title compound having the following physical data was given.

TLC: Rf 0.26 (chloroform:methanol=4:1); NMR: δ7.37–7.10 (11H, m), 7.06 (1H, t, J=8 Hz), 7.01 (1H, s), 6.80 (1H, d, J=8 Hz), 6.58 (1H, d, J=8 Hz), 5.34 (1H, s), 4.90 (1H, brs), 4.64 (2H, s), 4.22–4.08 (2H, m), 3.13–2.70 (3H, m), 2.45–2.12 (2H, m), 2.00–1.77 (1H, m), 1.75–1.53 (1H, m).

Formulation example 1

The following components were admixed in conventional method and punched out to obtain 100 tablets each containing 5 mg of active ingredient.

TABLE 7

| EX. No. | Structure of the example compound | NMR |
|---|---|---|
| 25(a) | (isoxazole structure with tetrahydronaphthalene, OCH₂CO₂H, and diphenylmethyl groups; O—N ring) | δ 7.40–7.10(12H, m), 6.80(1H, d, J=8Hz), 6.71(1H, d, J=8Hz), 5.82(1H, s), 5.54(1H, s), 4.63(2H, s), 3.03–2.10 (7H, m), 1.98–1.73(1H, m), 1.45–1.22(1H, m). |
| 25(b) | (isothiazole structure with tetrahydronaphthalene, OCH₂CO₂H, and diphenylmethyl groups; S—N ring) | δ 7.40–7.10(10H, m), 7.02(1H, t, J=8Hz), 6.80–6.55(4H, m), 5.67(1H, s), 4.64(2H, s), 3.03–2.30(6H, m), 2.22–1.85(2H, m), 1.50–1.21(1H, m). |

The example compounds shown in the table 7 are named as follows:

25(a)  [2-(3-Diphenylmethylisoxazol-5-yl)methyl-1,2,3,4-tetrahydronaphthalen-5-yloxy]acetic acid 25(b)  [2-(3-Diphenylmethylisothiazol-5-yl)methyl-1,2,3,4-tetrahydronaphthalen-5-yloxy]acetic acid

| | |
|---|---|
| [2-(4-((3-Pyridyl)phenylmethyl)pyrazol-1-yl)methyl-3,4-dihydronaphthalen-5-yloxy] acetic acid | 500 mg |
| Carboxymethylcellulose calcium | 200 mg |
| Magnesium stearate | 100 mg |
| Microcrystalline cellulose | 9.2 g |

Formulation example 2

The following components were admixed in conventional manner. The solution was sterilized in conventional manner, placed 5 ml portion into 10 ml ampoules and freeze-dried to obtain 100 ampoules each containing 2 mg of the active ingredient.

| | |
|---|---|
| [2-(4-((3-Pyridyl)phenylmethyl)pyrazol-1-yl)methyl-3,4-dihydronaphthalen-5-yloxy] acetic acid | 200 mg |
| Citric acid, anhydrous | 20 mg |
| Distilled water | 500 ml |

"While the invention has been described in detail and with reference to specific examples thereof, it will be apparent to one skilled in the art that various changes and modifications can be made therein without departing from the spirit and scope thereof."

What we claim is:

1. A fused benzeneoxyacetic acid derivative of the formula (I):

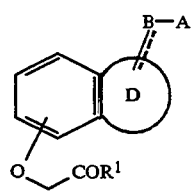
(I)

wherein 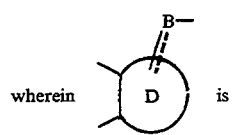 is

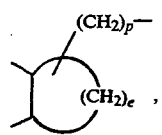 (i)

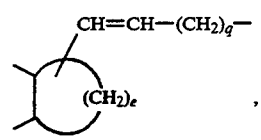 (ii)

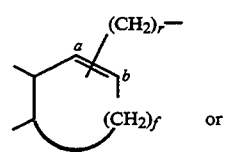 or (iii)

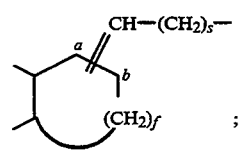 ; (iv)

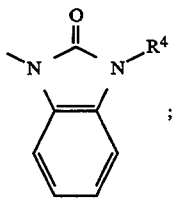

A is $R^1$ is
(i) a hydroxy group,
(ii) a $C_{1-12}$ alkoxy group, or
(iii) $NR^2R^3$;

$R^2$ and $R^3$ each, independently, is
(i) a hydrogen atom or
(ii) a $C_{1-4}$ alkyl group, or $R^2$ and $R^3$, taken together with the nitrogen atom bound to $R^2$ and $R^3$ are the residue of an amino acid;

$R^4$ is
(i) a hydrogen atom,
(ii) a $C_{1-4}$ alkyl group,
(iii) a phenyl group, or
(iv) a $C_{1-4}$ alkyl group substituted by 1 or 2 phenyl groups, wherein said phenyl group may be substituted by 1 to 3 of a $C_{1-4}$ alkyl group, a $C_{1-4}$ alkoxy group, a halogen atom, a nitro group or a trihalomethyl group, when $R^4$ is phenyl or the group containing phenyl;

e is 3–5;
f is 1–3;
p is 1–4;
q is 0–2;
r is 1–4;
s is 0–3;

with the proviso that
(1) q or s is not 0; and
(2) —(CH$_2$)$_r$13 or =CH—(CH$_2$)$_s$— are bonded to the carbon atom at a position a or b in the ring;

or non-toxic salts thereof or non-toxic acid addition salts thereof.

2. A compound according to claim 1, wherein $R^1$ is hydroxy.

3. A compound according to claim 1, wherein $R^1$ is $C_{1-12}$ alkoxy.

4. A compound according to claim 1, wherein $R^1$ is $NR^2R^3$.

5. A compound according to claim 1, wherein

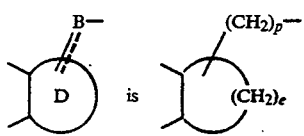

in which p and e are the same meaning as defined in claim 1.

6. A compound according to claim 1, wherein

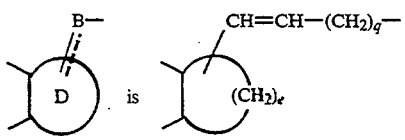

in which q and e are the same meaning as defined in claim 1.

7. A compound according to claim 1, wherein

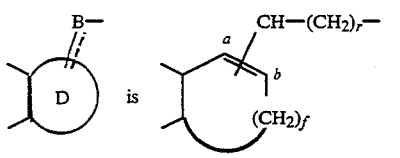

in which r, f, a and b are the same meaning as defined in claim 1.

8. A compound according to claim 1, wherein

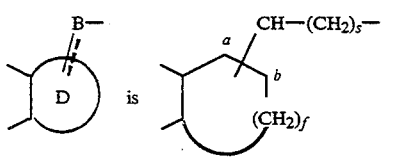

in which s, f, a and b are the same meaning as defined in claim 1.

9. A compound according to claim 1, wherein $R^4$ each, independently, is
(i) hydrogen atom,
(ii) $C_{1-4}$ alkyl,
(iii) phenyl or
(iv) $C_{1-4}$ alkyl substituted by one or two of phenyl.

10. A compound according to claim 9, which is:
(i) [2-(3-Phenyl-2-oxo-2,3-dihydrobenzimidazol-1-yl)methyl-1,2,3,4-tetrahydronaphthalen-5-yloxy]acetic acid, or
(ii) [2-(2-(3-Phenyl-2-oxo-2,3-dihydrobenzimidazol-1-yl)ethyl)-1,2,3,4-tetrahydronaphthalen-5-yloxy]acetic acid, or
(iii) a methyl ester, an octyl ester, an acetamide, or an amide with glycine of (i) or (ii) above.

11. A pharmaceutical composition which comprises, as active ingredient, an effective amount of a fused benzeneoxyacetic acid derivative of the formula (I) depicted in claim 1 or a non-toxic salt thereof, or a non-toxic acid addition salt thereof, with a pharmaceutical carrier or coating.

12. A method for the prevention and/or the treatment of thrombosis, arteriosclerosis, ischemic heart diseases, gastric ulcer or hypertention, which comprises the administration of an effective amount of a fused benzeneoxyacetic acid derivative of the formula (I) depicted in claim 1 or a non-toxic salt thereof, or a non-toxic acid addition salt thereof.

* * * * *

UNITED STATES PATENT AND TRADEMARK OFFICE
CERTIFICATE OF CORRECTION

PATENT NO.   : 5,389,666
DATED        : February 14, 1995
INVENTOR(S)  : Nobuyuki Hamanaka, Kanji Takahashi, Hidekado Tokumoto It is certified that error(s) appears in the above-identified patent and that said Letters Patent is hereby corrected as shown below:

Column 84, line 1, insert --A is--; and

Column 84, line 11, delete "A is".

Signed and Sealed this

Thirtieth Day of June, 1998

Attest:

BRUCE LEHMAN

Attesting Officer

Commissioner of Patents and Trademarks